US012791550B2

(12) United States Patent
Staack et al.

(10) Patent No.: US 12,791,550 B2
(45) Date of Patent: Nov. 10, 2026

(54) BREATH CAPTURE AND ANALYSIS SYSTEM AND METHOD

(71) Applicants: The Texas A&M University System, College Station, TX (US); Worlds Enterprises, Inc., Dallas, TX (US)

(72) Inventors: David Staack, College Station, TX (US); Daniel Arthur McAdams, II, College Station, TX (US); Matthew Leonard Burnette, Bryan, TX (US); Devesh Bhasin, College Station, TX (US); Xin Tang, College Station, TX (US); Maulik Kotecha, College Station, TX (US); Kavita Rathore, Bryan, TX (US); Christopher Campbell, College Station, TX (US); Jason G. Fox, Dallas, TX (US); Paul Michael Aarseth, Dallas, TX (US)

(73) Assignees: The Texas A&M University System, College Station, TX (US); Worlds Enterprises, Inc., Dallas, TX (US)

( * ) Notice: Subject to any disclaimer, the term of this patent is extended or adjusted under 35 U.S.C. 154(b) by 339 days.

(21) Appl. No.: 18/275,250

(22) PCT Filed: Feb. 2, 2022

(86) PCT No.: PCT/US2022/014924

§ 371 (c)(1),
(2) Date: Aug. 1, 2023

(87) PCT Pub. No.: WO2022/169860

PCT Pub. Date: Aug. 11, 2022

(65) Prior Publication Data

US 2024/0133867 A1 Apr. 25, 2024
US 2024/0230624 A9 Jul. 11, 2024

Related U.S. Application Data

(60) Provisional application No. 63/280,725, filed on Nov. 18, 2021, provisional application No. 63/145,409, filed on Feb. 3, 2021.

(51) Int. Cl.
*G01N 33/497* (2006.01)

(52) U.S. Cl.
CPC ....... *G01N 33/497* (2013.01); *G01N 33/4977* (2024.05)

(58) Field of Classification Search
None
See application file for complete search history.

(56) References Cited

U.S. PATENT DOCUMENTS 6,726,637 B2 4/2004 Phillips
8,347,688 B2 1/2013 O'Brien
(Continued)

OTHER PUBLICATIONS

Extorr; Residual Gas Analyzer Introduction ; https://www.extorr.com/Misc/ResidualGasAnalyzerIntroductionMay21-2020.pdf; 2020 (Year: 2020).*

*Primary Examiner* — Jay B Shah
(74) *Attorney, Agent, or Firm* — Jackson Walker LLP

(57) ABSTRACT

A breath capture and analysis system includes a breath inlet for capturing a user's breath. The breath is drawn into the system and retained for analysis. The system includes a membrane that allows volatile organic compounds contained in the breath to pass therethrough. The volatile organic compounds pass into a vacuum chamber that includes a residual gas analyzer that is configured to analyze the volatile organic compounds. The analyzed breath is then vacated from the system.

6 Claims, 16 Drawing Sheets

(56) References Cited

U.S. PATENT DOCUMENTS

| | | | |
|---|---|---|---|
| 9,918,661 | B2 | 3/2018 | Cormier et al. |
| 2018/0214050 | A1 | 8/2018 | Purves |
| 2019/0271685 | A1 | 9/2019 | Haick et al. |
| 2019/0307396 | A1 | 10/2019 | Attariwala et al. |
| 2020/0309753 | A1 | 10/2020 | Mamerow et al. |
| 2022/0034854 | A1 * | 2/2022 | Chen ...................... A61B 10/00 |

* cited by examiner

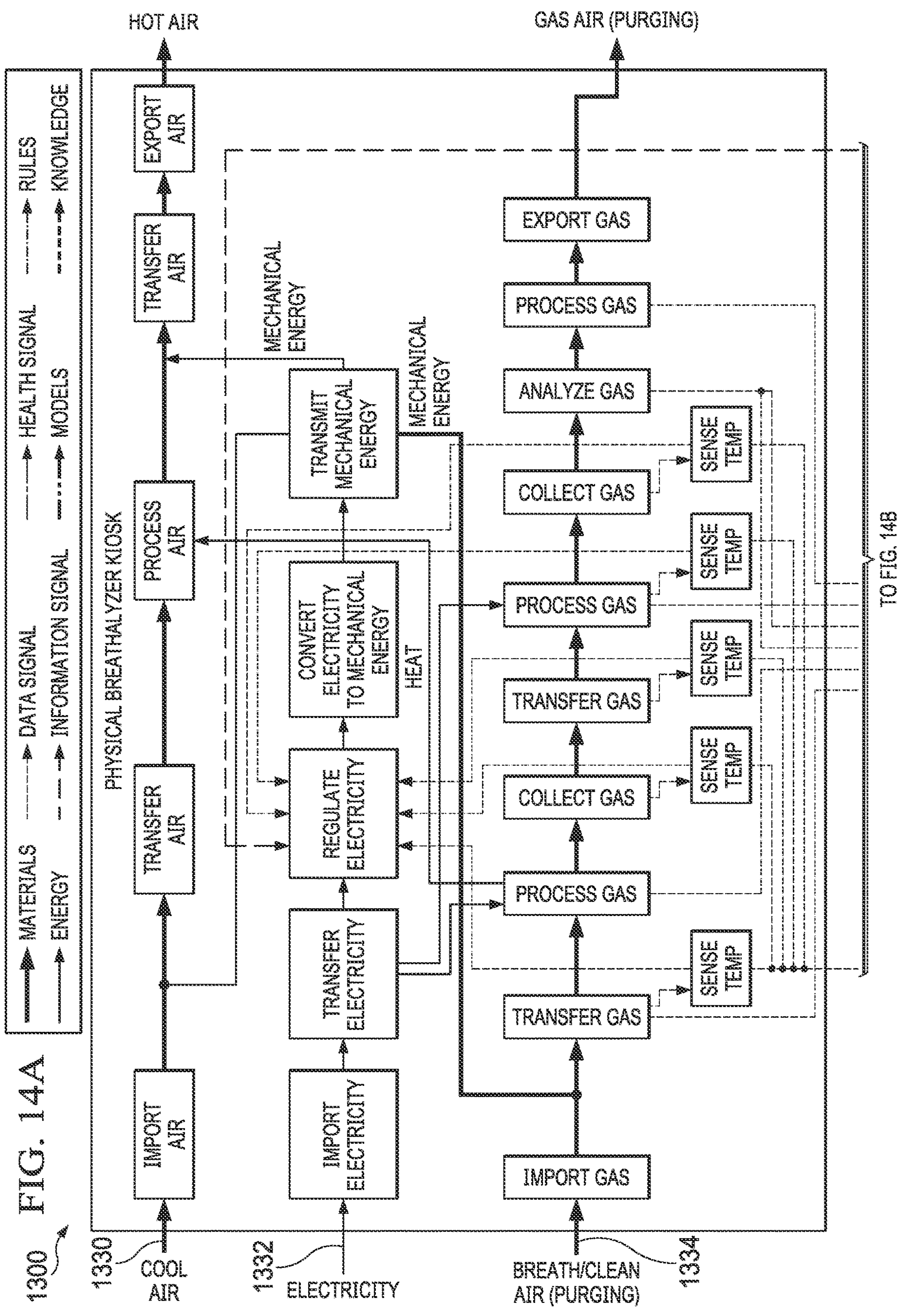
FIG. 14A
1300
MATERIALS
ENERGY
DATA SIGNAL
INFORMATION SIGNAL
HEALTH SIGNAL
MODELS
RULES
KNOWLEDGE
PHYSICAL BREATHALYZER KIOSK
HOT AIR
GAS AIR (PURGING)
IMPORT AIR
TRANSFER AIR
PROCESS AIR
TRANSFER AIR
EXPORT AIR
IMPORT ELECTRICITY
TRANSFER ELECTRICITY
REGULATE ELECTRICITY
CONVERT ELECTRICITY TO MECHANICAL ENERGY
TRANSMIT MECHANICAL ENERGY
MECHANICAL ENERGY
MECHANICAL ENERGY
HEAT
IMPORT GAS
TRANSFER GAS
PROCESS GAS
COLLECT GAS
TRANSFER GAS
PROCESS GAS
COLLECT GAS
ANALYZE GAS
PROCESS GAS
EXPORT GAS
SENSE TEMP
SENSE TEMP
SENSE TEMP
SENSE TEMP
SENSE TEMP
TO FIG. 14B
1330
COOL AIR
1332
ELECTRICITY
1334
BREATH/CLEAN AIR (PURGING)

BREATH CAPTURE AND ANALYSIS SYSTEM AND METHOD

CROSS-REFERENCE TO RELATED APPLICATIONS

This patent application claims priority to, and incorporates by reference the entire disclosure of, U.S. Provisional Patent Application No. 63/145,109, filed on Feb. 3, 2021; and U.S. Provisional Patent Application No. 63/280,725, filed on Nov. 18, 2021.

TECHNICAL FIELD

The present disclosure relates generally to testing for disease and infectious pathogens and more particularly, but not by way of limitation, to a device for capturing a user's breath and distributing the user's breath through a detector for analysis.

BACKGROUND

This section provides background information to facilitate a better understanding of the various aspects of the disclosure. It should be understood that the statements in this section of this document are to be read in this light, and not as admissions of prior art.

Effective management and containment of infectious pathogens requires accurate and expedient testing of suspected cases so that mitigation measures, such as isolation or quarantine, can be put in place. In cases of a wide-spread pandemic illness, such as COVID-19, the volume capacity for testing must be sufficient to address the number of suspected cases. In all cases, the test must be capable of detecting the presence of the pathogen and providing results in sufficiently short timeframe to limit the potential for post-testing transmission of the pathogen. Current testing protocols typically utilize single-use items such as, for example, a nasal or oral swab, which are then subjected to a chemical test, which indicates the presence of the pathogen. The swabs and chemical solutions used in the present style of testing are consumable components that must be manufactured and distributed in quantities sufficient to meet demand. Additionally, present testing methodologies are slow to produce a result, often requiring several days. Such a timeframe does not provide confirmation of infection in a timeframe sufficient to prevent transmission of the pathogen. Breath contains various components: endogenous, exogenous and environmental. This includes volatile organic compounds and exhaled droplets and particles. The endogenous source of these in the breath are by equilibration commensurate with various blood bore compounds. Environmental compounds toxic or benign) may absorb into the lung tissue or blood and be exhaled over significant duration after exposure. Infection in the body or lungs may also lead to pathogenic origin or modification to the typical metabolism of healthy cells. All of these compounds may indicate infection from a pathogen (minor, acute, short-term, and/or chronic) and or disease (e.g. diabetes, cancer).

SUMMARY

Aspects of the disclosure relate to a breath capture and analysis system. The breath capture and analysis system includes a breath inlet coupled to a cylinder. A piston is disposed in the cylinder. The piston is actuated by a linear actuator. A long retention time flow path is coupled to the cylinder. A membrane is exposed to the long retention time flow path. The membrane allows passage of volatile organic compounds therethrough. The membrane and flow conduit system are at a controlled and programmable temperature and pressure to facilitate the concentration and isolation of specific compounds. A detector is coupled to the capture and concentration system. In various embodiments, the detector is a vacuum chamber coupled to the membrane and a residual gas analyzer disposed in the vacuum chamber. A turbomolecular and roughing pump is coupled to the vacuum chamber.

Aspects of the disclosure relate to a method of capturing and analyzing a user's breath. The method includes receiving a user's exhaled breath into a breath inlet. A piston draws the exhaled breath into a cylinder and the exhaled breath is held in the cylinder. The piston expels the exhaled breath from the cylinder into a long retention time flow path. The long retention time flow path is exposed to a membrane. The membrane allows selective passing of volatile organic compounds therethrough. An active heating and cooling temperature control system modulates the flow of selected compounds through the selective membrane or concentrator and to the detector. Volatile organic compounds are selectively passed through or released from the membrane and into the detector chamber. In various embodiments, a residual gas analyzer in a vacuum chamber analyses the volatile organic compounds in the vacuum chamber. In another embodiment a secondary ion mass spectrometer at moderately low pressure is the detector. In another embodiment the sensor may be a MEMS based humidity, temperature and VOC sensor (ex. Bosch BME688). In another embodiment multiple sensor inputs can provide correlated qualitative and quantitative information on the breath and VOCs present. Results of the analysis are transmitted to the user.

This summary is provided to introduce a selection of concepts that are further described below in the Detailed Description. This summary is not intended to identify key or essential features of the claimed subject matter, nor is it to be used as an aid in limiting the scope of the claimed subject matter.

BRIEF DESCRIPTION OF THE DRAWINGS

A more complete understanding of the subject matter of the present disclosure may be obtained by reference to the following Detailed Description when taken in conjunction with the accompanying Drawings wherein.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Figure 1:
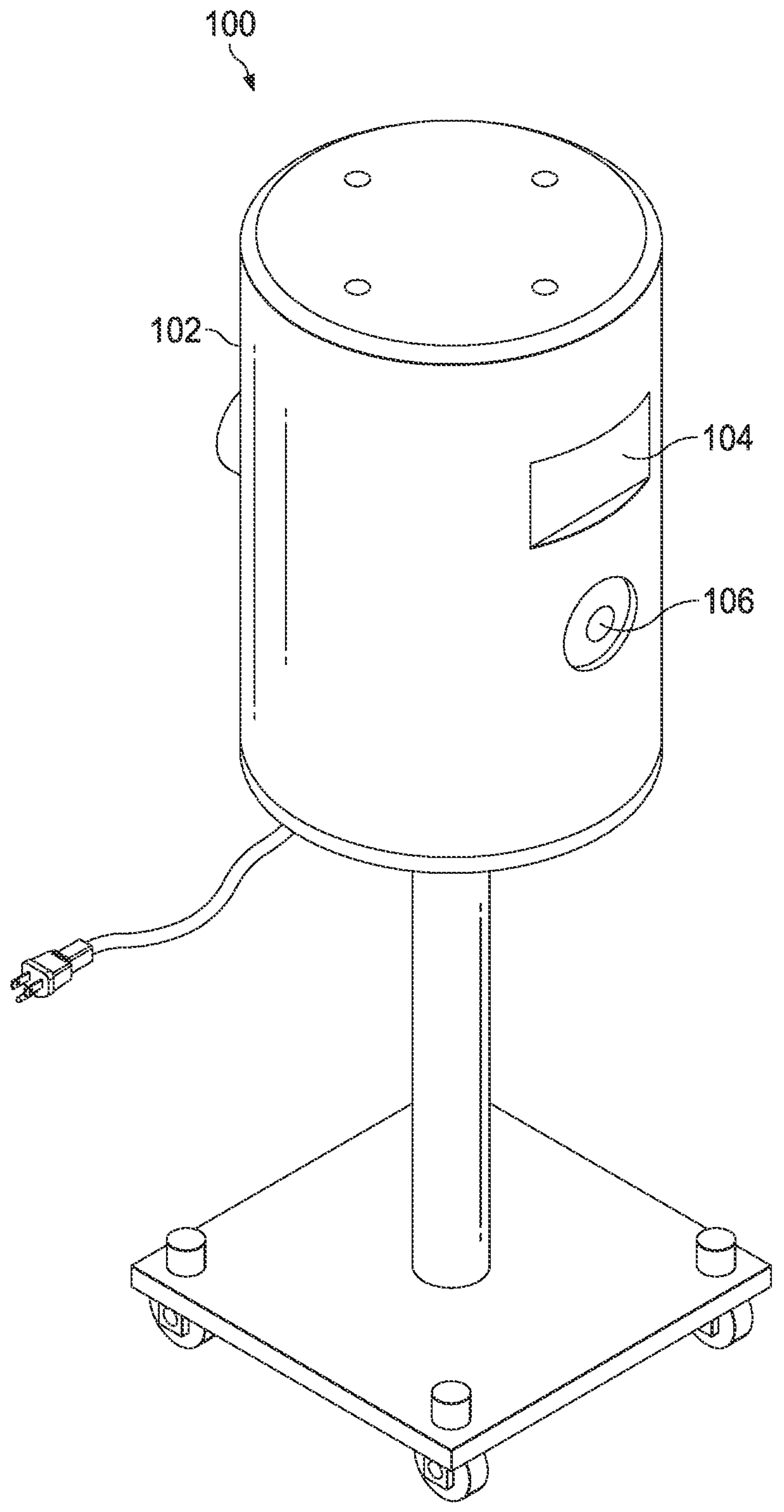
FIG. 1 is a cross-sectional view of a breath capture and analysis system according to aspects of the disclosure.

FIG. 1 is a side view of a breath capture and analysis system 100. The breath capture and analysis system 100 includes a shell 102 that conceals the interior of system 100, a breath inlet 106, and an interface 104. In various embodiments, the breath inlet 106 is constructed of, for example, copper and is heated to approximately 100° C. The material of the breath inlet 106 and the temperature facilitate decontamination of an exterior surface of the breath inlet 106. In various embodiments, the temperature of the breath inlet 106 prevents condensation and ensures that gaseous components of a user's breath such as, for example, water vapor and volatile organic compounds (VOCs) remain in a gaseous state. In various embodiments, the temperature is also used to volatize and exhaled droplets and entrapped compounds and biological components within such droplets. In various embodiments, the interface 104 is a touch-free interface (e.g., a display screen) that provides step-by-step instructions to the user for use. The decontamination of the exterior surface of the breath inlet may be facilitated via mechanisms other than heated copper material such as, ultra-violate rays.

FIG. 2 is a schematic diagram of the breath capture and analysis system 100. The breath capture and analysis system 100 includes a breath capture system 202 and an analytical system 204. The breath capture system 202 includes the breath inlet 106. The breath inlet 106 is fluidly coupled to a cylinder 206 via a primary inlet line 208. An inlet check valve 210 is disposed in the primary inlet line 208. The inlet check valve 210 allows flow of fluid from the breath inlet 106 into the cylinder 206 and prevents back flow of fluid from the cylinder 206 towards the breath inlet 106. In various embodiments, the primary inlet line 208 is constructed of, for example, copper and is heated to approximately 100° C. However, in various embodiments, the primary inlet line 208, or portions of the primary inlet line 208, may be constructed of a flexible, high temperature material such, as for example, a high-temperature polymer to facilitate flow routing. In a particular embodiment, such a high-temperature polymer may be, for example, polytetrafluoroethylene, sold under the name Teflon by The Chemours Company of Wilmington, DE.

Still referring to FIG. 2, the cylinder 206 includes a piston 212 that is moved by a linear actuator 214. The speed of the linear actuator 214 can be varied, for example, by changing a driving voltage and pulse width modulation. In various embodiments, the driving voltage of the linear actuator 214 during breath intake is approximately 15V, which draws in a breath from the user at approximately 6 L/min for approximately 8 seconds. During injection of the breath into the analytical system 204, the driving voltage of the linear actuator 214 is approximately 3.5 V, which injects the breath to the analytical system 204 at approximately 1 L/min over approximately 50 seconds. The drawing in of breath can be timed to the duration of the user's exhalation. The volume of the cylinder 206 is approximately 0.8 L; however, the volume could be increased to capture the user's entire breath (~2 L) or decreased to make a more compact system. In embodiments utilizing smaller volumes of the cylinder 206, the duration of drawing in the breath is comparable to the duration of exhalation of the user. This ensures that all segments of the exhalation (including the last portion of the user's breath, which is higher in VOC) is captured. The cylinder 206 is coupled to a three-way valve 216 via a flow line 218. An outlet check valve 220 is disposed in the flow line 218. The outlet check valve 220 allows flow of fluid from the cylinder 206 towards the three-way valve 216 and prevents back flow of fluid from the three-way valve 216 towards the cylinder 206. In various embodiments, the cylinder can be replaced by another controllably deformable volume such as a bellows, balloon, or bag such that the volume can be varied controllably and the temperature can be controlled for volatization and decontamination. The linear actuator 214 can be replaced by hydraulic or pneumatically controlled mechanisms, or non-linear actuators.

Still referring to FIG. 2, the three-way valve 216 controls whether fluid flows into the analytical system 204 is from the breath capture system 202 or from an alternate source. In various embodiments, the alternate source is, for example, an alternate inlet port 222 that is located on the back of the breath capture and analysis system 100. In various embodiments, an ambient sampling of air can be drawn in through the alternate inlet port 222. Also, the alternate inlet port 222 can be used to inject breath captured in a container such as, for example, a tevlar or similar bag or sampling container. In various embodiments, the alternate inlet port 222 may be used to inject standards for calibration of the breath capture and analysis system 100. The alternate inlet port 222 may also be used to purge a user's breaths from the breath capture and analysis system 100. In various embodiments, the alternate inlet port 222 may be used, for example, for passive sampling of the environment. In addition to analyzing specific breath exhalations the breath capture and analysis system 100 may, in various embodiments, be used to monitor background chemicals in ambient air. Such a functionality could be utilized to, for example, detect a biowarfare agent, a new VOC from some contamination source, or, at higher sensitivity, a VOC from a sick person in the room who did not directly breath into the breath capture and analysis system 100.

Still referring to FIG. 2, fluid flow from the breath capture system 202 or from the alternate inlet port 222 are passed over a membrane 224 along a long retention time flow path 226. The long retention time flow path 226 includes a spiral-shaped tube that abuts the membrane 224. In various embodiments, the long retention time flow path 226 is approximately 3/32" wide, approximately 4" long, and spirals around on the face of a pipe fitting such as, for example, a DN40 fitting. The membrane 224 is selective and the rate of flow of VOC through the membrane is higher than the rate of flow of, for example, $N_2$, $CO_2$, $O_2$, $H_2O$ and other high-concentration air components. Thus, the membrane 224 can increase the sensitivity of the analytical system 204 to VOC. The back of the membrane 224 is fluidly coupled to a vacuum chamber 225. The front of the membrane 224 is exposed to the airflow from the breath capture system 202. The passage of the selective VOC through the membrane 224 is can be termed elution. Each VOC compound has a different elution time. The selectivity of elution time to compound is an important discriminator in identifying or at least telling apart different VOC. The membrane 224 and long retention time flow path 226 are currently part of a membrane assembly.

Figure 2A:
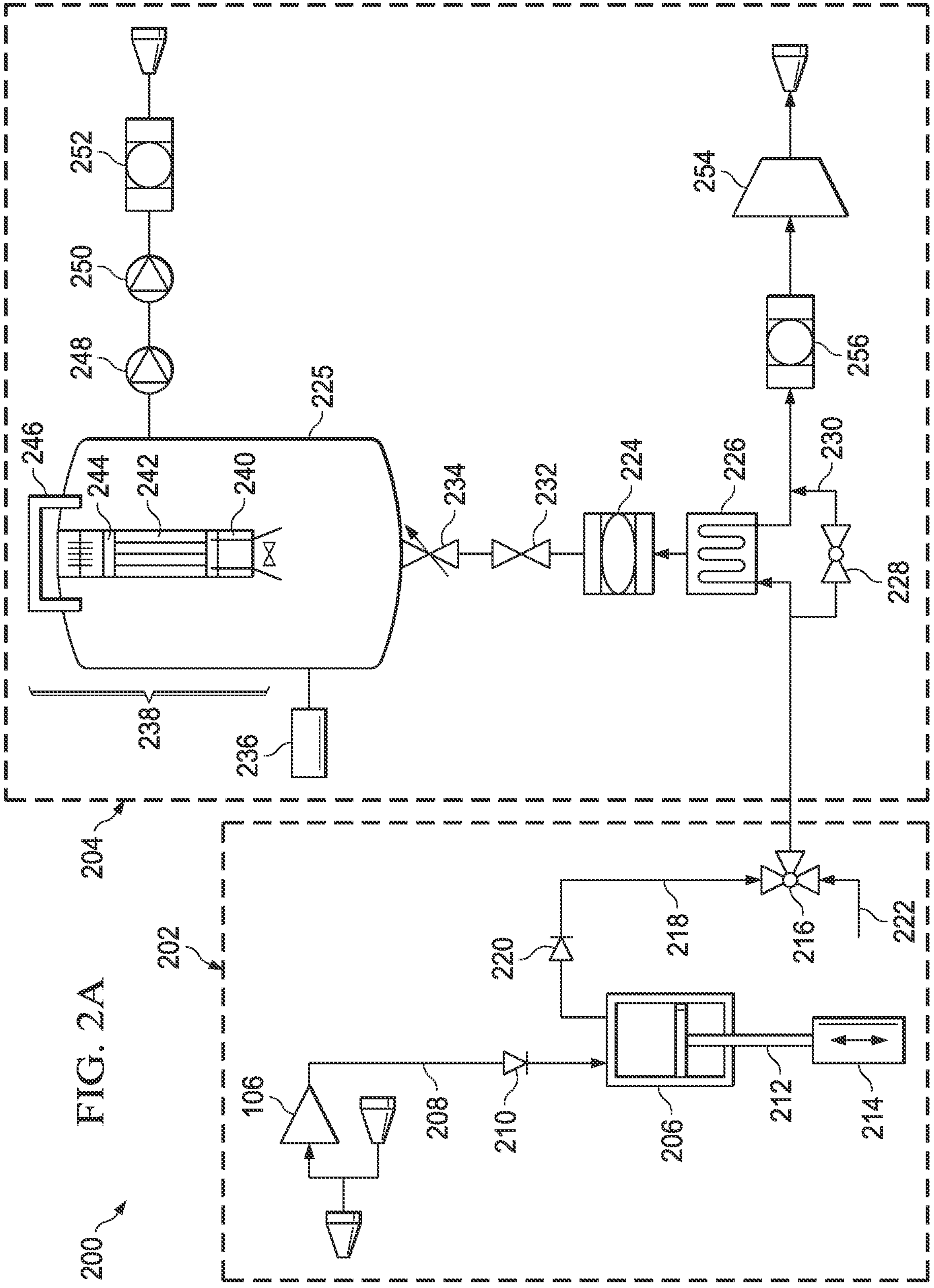
FIG. 2A is a schematic diagram of a breath capture and analysis system according to aspects of the disclosure.
Figure 2B:
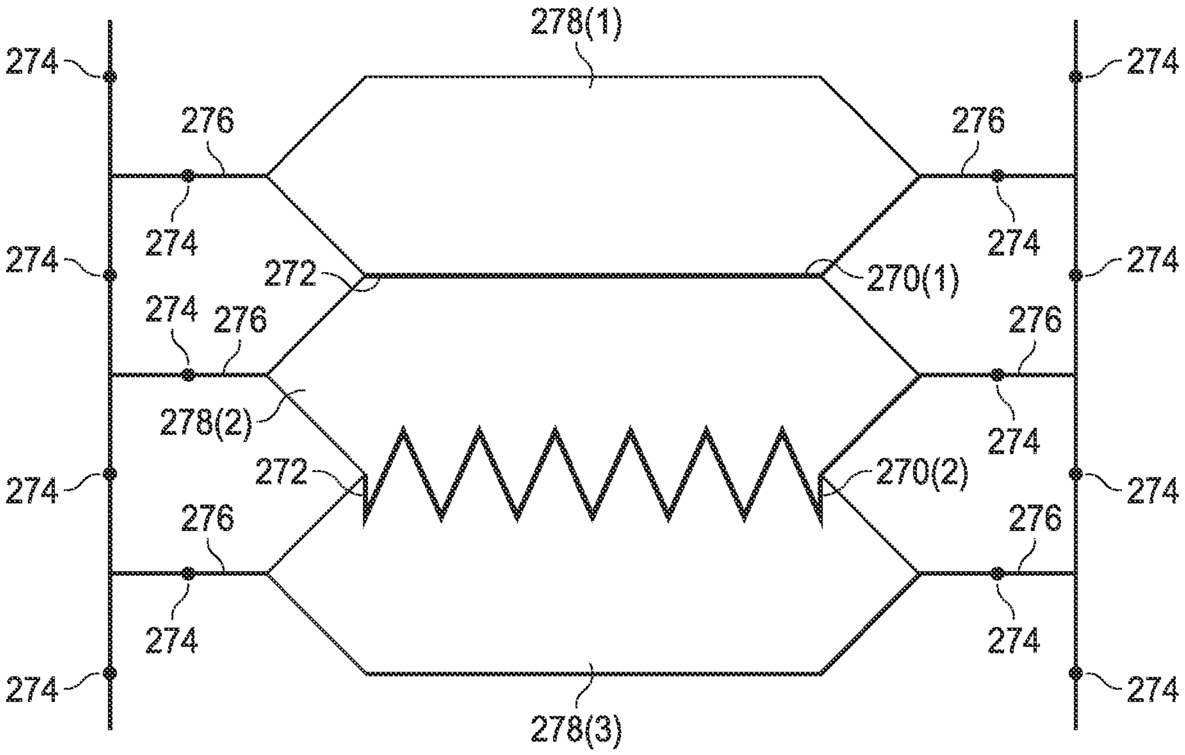
FIG. 2B is a flow a schematic diagram illustrating a reconfigurable serial/parallel membrane/sorbent materials and analyte control volumes leading from capture system to detector.

Referring to FIG. 2B, the membrane flow path may be a compact volume, high surface area membrane consisting of repeating parallel flow structures such as tubules or folded structures. The high area allows for a higher flow rate transmission of VOC through the selective membrane and toward the analytical system 204. In various embodiments, multiple selective membranes 270(1)-270(2) could be arranged in series to further concentrate the analytes. In various embodiments, a thermal management system controls a temperature of the membrane that can be attained by various techniques including: conductive heating and cooling through the membrane holder walls 272 using, for example, resistive heaters and thermoelectric heaters and coolers; convective heating using a cooling fluid (such as, for example, water or glycol) for rapid heat transfer; or through radiative heating of the membrane surface using, for example, LED, laser or similar intense light sources. Multiple on/off microvalves 274 are disposed in the flow path streams 276 so that flows from separate analyte volumes 278(1)-278(3) can be directed to the analytical system 204. Membrane materials and absorbents placed in the volumes can increase selectivity to targeted VOC. These membranes 270(1)-270(2) can be staged flow through them controlled with microvalves 274 through membrane selection and staged adsorption, permeation, and desorption processes the various VOC can be retained, concentrated, and selectively released to the detectors. Samples may also be conveniently and rapidly purged and flushed.

Referring again to FIG. 2A, a bypass valve 228 is disposed in a bypass flow line 230. The bypass valve 228 when open allows for a more rapid flow of air through the breath capture and analysis system 100. The bypass valve 228 is opened when either a lower pressure drop is required across the membrane 224 or when a higher flow rate through the breath capture system 202 is needed. In various embodiments, a high flow rate through the breath capture system 202 is useful to purge a sample from the breath capture and analysis system 100.

Still referring to FIG. 2A, flow of fluid into the vacuum chamber 225 is limited by a vacuum choke 232. In various embodiments, the vacuum choke 232 may be constructed in the form of an orifice placed between the membrane 224 and vacuum chamber 225 to limit the fluid flow rate into the vacuum chamber 225. In various embodiments, the membrane 224 can act as a vacuum choke as the membrane 224 has a nano-porous structure. Also sealing around the edge of the membrane 224 may act as the gas flow choke. In various embodiments, a high enough flow rate into the vacuum chamber 225 is needed so that the time response of the analytical system 204 is comparable to the time diagnostic and the breath capture system 202. In the vacuum chamber 225 an analytical scan is performed about every 3-4 seconds. The pressure in the vacuum chamber 225 is approximately 0.5E-5 Torr to approximately 10E-5 torr and the fluid flow rate at pressure into the vacuum chamber 225 is about 30 to 90 L/min. These are very small mass flow rates through the membrane 224. A gate valve 234 is fluidly coupled to the vacuum chamber 225 and to the membrane 224. In various embodiments, the gate valve 234, when closed, isolates the vacuum chamber 225 and allows pressure inside the vacuum chamber 225 to be maintained during cleaning or replacement of the membrane 224. A pressure gauge 236 is fluidly coupled to the vacuum chamber 225 so as to be exposed to the internal pressure of the vacuum chamber 225. In various embodiments, a Pirani or similar high-vacuum gauge is useful to monitor both the pumping down and operational pressure of the vacuum chamber 225. The pressure of the vacuum chamber 225 should be within a preferred range both for sensitivity of the device and lifetime of the components.

Still referring to FIG. 2A, a residual gas analyzer (RGA) 238 is disposed in the vacuum chamber 225. The RGA 238 includes an ionizer 240, a quadrapole 242, a multiplier, and a detector 244, arranged in a configuration of a mass spectrometer 246. The RGA 238 measures concentration or partial pressure as a function of atomic mass. A 70 eV electron beam is generated in the ionizer 240 and bombards molecules present in the vacuum system. The ions and generated ion fragments of the molecules are accelerated into the quadrapole 242. In various embodiments, the quadrapole 242 is powered by an RF frequency to selectively allow a particle having a specific mass-to-charge (M/Z) ratio to pass through. The detector 244 is disposed at the far end of the quadrapole 242 and, in various embodiments, operates with a multiplier for improved sensitivity. In various embodiments the RGA 238 may take approximately 3 to approximately 4 seconds to scan from 1 to 200 AMU. This represents a dwell time of about 16 ms per AMU. With a breath injected into the breath capture system 202 over 50 seconds, this represents approximately 14-15 scans per breath with some additional scans as the VOC elute through the membrane 224. The detector 244 combined with the membrane 224 and combine with the breath capture system 202 is thus able to produce a signal vs AMU vs elution time multidimensional characteristic of the breath and air samples. Comparison of the 3-dimensional data set (signal×amu×time) for a breath and comparison to ambient air allows for identification of unique characteristics of the breath. These characteristics can be correlated with characteristics of the user providing the breath such as, for example, health, viral infection, smoking, coffee drinking, and other characteristics. In various embodiments, specific biomarkers could be identified for specific diseases; however, in other embodiments, this is accomplished through trained artificial intelligence (AI) algorithms.

The ionizer, multiplier, and RF setting can be altered to specifically target specific molecule types. For example, reducing the ionizer electron beam voltage to 40 eV increases the RGA sensitivity to high molecular weight compounds such as the VOC of interest with decreasing sensitivity to smaller compounds like common air components. Sensitivity can be further increased by operating the ionizer at a lower beam current to reduce the background plasma density in the vacuum chamber and improve signal to noise ratio. The multiplier voltage settings can also be optimized to the detection of higher molecular weight species improving overall signal to noise ratios for 50-300 AMU molecules and fragments while sacrificing sensitivity to lower molecular weight species. For example, a multiplier voltage of 1850 V can have an 8 fold increase in SNR compared to a voltage of 1150 V for molecules of 78 AMU but a significant (>10 fold) decrease in the sensitivity to 18 AMU molecules.

AI training the multidimensional data set for a breath sample is compared to the results of an independent diagnostics. Dimensional aspects of the data might include, time, AMU (for mass spectrometers), ionizer voltage (for mass spectrometers), detector(s) signal level, membrane temperature, sorbent material, membrane material and area, and analyte volume (controlled by valve states). For example, breaths could be taken from subjects who test positive and subjects who test negative for various pathogens such as, for example, COVID-19. Correlation of the macro and micro features of the whole data set can be correlated with results from, for example, a polymerase chain reaction (PCR) test. From a training set the AI can then compare an unknown sample to the training set and determine if the unknown sample better correlates with a negative test result or a positive test result. Such an AI is best trained with a high-quality PCR gold-standard test. The signal-time-AMU data set may need to be manipulated such as, for example, normalized or background subtracted prior to analysis by the AI. In various embodiments, the breath capture system 202 helps to ensure that the breaths injected into the mass spectrometer 246 and or RGA 238 to receive a more regular sample. A human directly exhaling into the analytical system 204 might have a variable duration and strength breath. When the breath capture system 202 injects the sample into the analytical system 204, the breath is always the same duration and strength.

Still referring to FIG. 2A, a turbo pump 248 is coupled to the vacuum chamber 225. In various embodiments, the turbo pump 248 is a compact yet high flow rate and high vacuum attaining pump. A roughing pump 250 is fluidly coupled to the turbo pump 248. In various embodiments, the turbo pump 248 cannot exhaust at ambient pressure and needs the roughing pump 250 to operate. In various embodiments, the turbo pump 248 and the roughing pump 250 should be oil free. The exhaust from the roughing pump 250 may be exhausted to ambient through a filter 252. Along the lines of oil free, all components of the system can be chosen to be oil, lubricant free and low outgassing. For example, greased buna-N gasket on the piston cylinder can be replaced with oil free and lubricious Teflon gaskets. This minimizes machine induced VOC contamination.

The bypass flow line 230 and long retention time flow path 226 both lead into a sampling pump 254. The sampling pump 254 is used to draw air from the alternate inlet port 222 and to draw the air through the breath capture system 202. The sampling pump 254 flushes out breaths from the breath capture system 202 and flow clean air through the breath capture system 202 and the analytical system 204 for background data collection. A small particle filter 256 is on the outlet of the sampling pump 254. The filter 256 is necessary to prevent any biological contaminants in the breath from being pumped out into the ambient environment. In various embodiments, the filter 256 is a 0.03 μm filter at the back of the shell 102.

All of the components are kept warm to prevent condensation of VOC and water. In various embodiments, heating also sanitizes the device flow paths. The copper inlet is at 100° C., the breath capture system 202 is at approximately 100° C., the membrane 224 is at approximately 100° C. The vacuum chamber 225 is kept at approximately 60° C. to approximately 100° C. Other common sterilization techniques such as UV light (for surface) and ozone injection could also be used.

Operation of the breath capture and analysis system 100 will now be described relative to FIG. 2A. Prior to a user using the breath capture and analysis system 100, the three-way valve 216 is set to sample ambient air from the alternate inlet port 222. The bypass valve 228 is open and the sampling pump 254 is turned on. Such an arrangement allows a relatively clean background signal to be attained. The user comes to the breath capture and analysis system 100 and, after checking in, exhales into the breath inlet 106. In various embodiments, the user exhales into the breath inlet 106 through a straw. While the user is exhaling, the piston 212 is drawn down thereby taking in a breath. The three-way valve 216 is selected to sample ambient air through the alternate inlet port 222 and the sampling pump 254 is turned off. The timing of the breath intake is such that the draw time is comparable to the duration of an exhalation. In various embodiments, the breath capture and analysis system 100 emits a noise when the breath is being drawn. It has been found that emission of a noise is useful as the user tries to exhale during the whole duration of the noise and typically fully exhales their breath (including the VOC at the bottom of their lung). After the user is finished exhaling the breath is held within the cylinder 206. The user can now leave; however, analysis of the breath has not yet begun.

After a wait of approximately 1 second, the three-way valve 216 is switched to allow flow from the cylinder 206 to the membrane 224. The bypass valve 228 is closed and the sampling pump 254 is turned off. The piston 212 is set to push the breath sample from the cylinder 206 to the long retention time flow path 226. Typically, the breath is expelled from the cylinder 206 by the piston over approximately 50 to 300 seconds. During this time, the signals on the RGA 238 show a rapid increase in water vapor and $CO_2$, which are major components of a breath. The membrane 224 also begins to let VOC through and there is a slow increase in the signature of VOC in the mass spectrometer 246. After approximately 50 to 300 seconds the piston 212 is positioned such that the cylinder 206 is at minimum volume. In various embodiments, the cylinder 206 has a minimum volume of approximately 0.05 L and a maximum volume of approximately 0.8 L. The duration of this injection is chosen commensurate with the elution time of various target VOC through the membranes. These times can be measured and controlled through temperature control of the membrane to maximize the signal for a specific target compound. A compromise on injection time is chosen to maintain a high signal level target VOC separation, while still having a short overall analysis time for rapid sequential testing and reporting of results to subjects.

After the breath is expelled from the cylinder 206 to the long retention time, large surface area flow path 226 and the membrane 224, a flush of the breath capture system 202 is begun. The linear actuator 214 on the piston 212 is stopped and the sampling pump 254 is turned on. The bypass valve 228 is still closed and the three-way valve is set to allow flow from the cylinder 206. During this phase, the $CO_2$ and $H_2O$ peaks rapidly fall. However, the VOC peaks continue to rise as they elute and diffuse through the membrane 224 from the high-pressure side to the low-pressure side. They rise and then fall as the fresh air passed over the high-pressure side of the membrane 224. In various embodiments, the flush lasts approximately 50 seconds. Following the flush, the VOC, $H_2O$ and $CO_2$ peaks return to 'normal', pre-test levels.

After the flush, the breath capture and analysis system 100 is in the initial state. The bypass valve 228 is opened and the three-way valve 216 is set to sample from the alternative inlet port 222. In various embodiments, after an extended idle time the sampling pump 254 may be turned off. Turning off the sampling pump 254 prevents the filter 256 from becoming overly fouled.

Figure 3A:
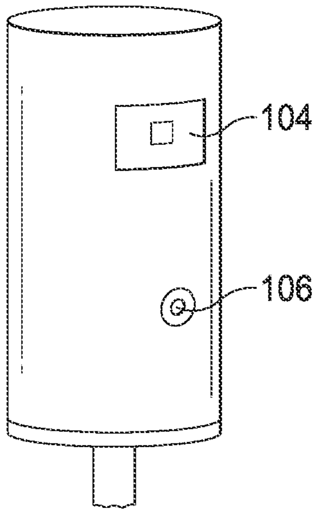
FIGS. 3A-3C are illustrations demonstrating use of a breath capture and analysis system according to aspects of the disclosure.
Figure 3B:
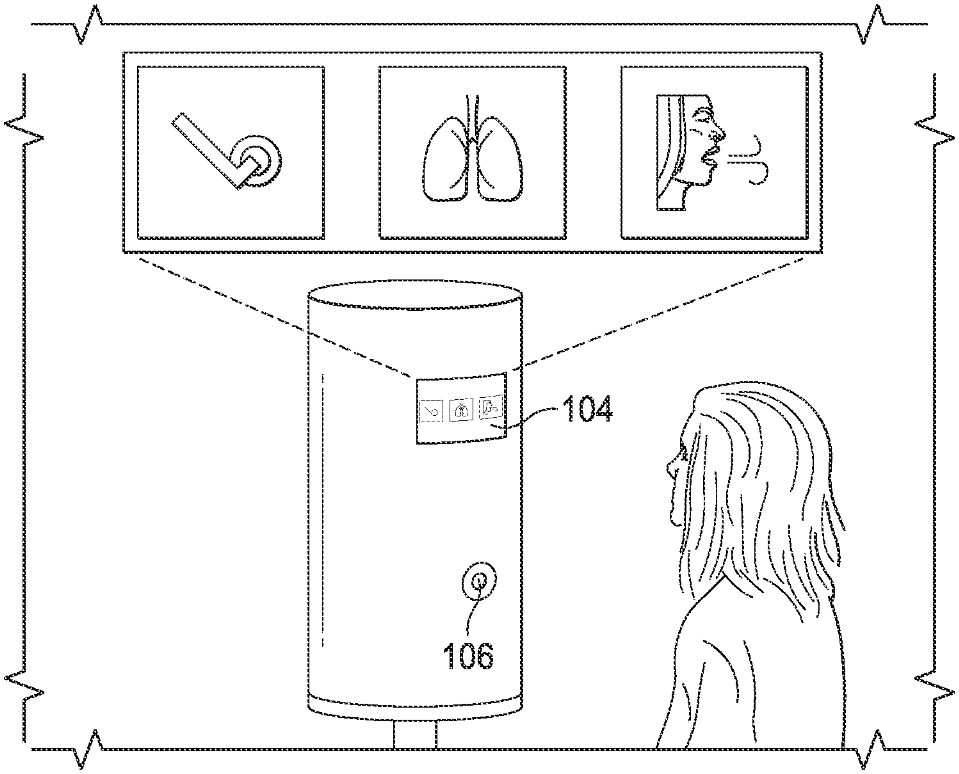
Figure 3C:
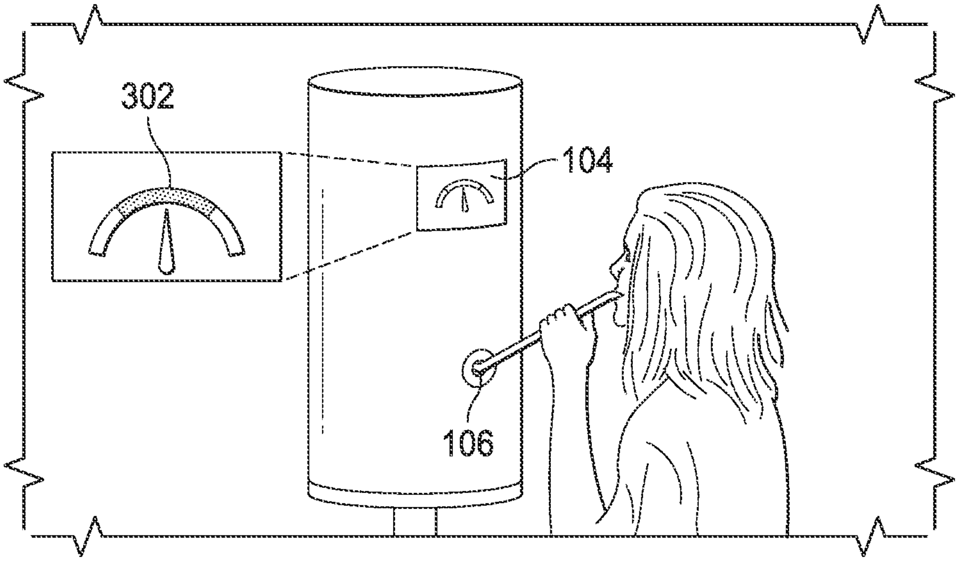

FIGS. 3A-3C are illustrations demonstrating use of the breath capture and analysis system 100. As illustrated in FIGS. 3A-3C, the breath capture and analysis system 100 includes the interface 104 and the breath inlet 106 that are formed in the shell 102. In various embodiments, the interface 104 communicates instructions and/or feedback to the user. As shown in FIG. 3B, in various embodiments, the interface 104 may first provide an instruction to, for example, "place a straw into the inlet", thereby prompting the user to place a straw into the breath inlet 106. In various embodiments, the interface 104 may prompt the user to, for example, "take a deep breath" and "blow firmly into the straw". As shown in FIG. 3C, while the user is exhaling into the breath inlet 106 via the straw, the interface 104 may provide a visual indication 302 of a sufficiency of the user's exhalation thereby notifying the user when an adequate amount of breath has been captured by the breath capture and analysis system 100.

Figure 4:
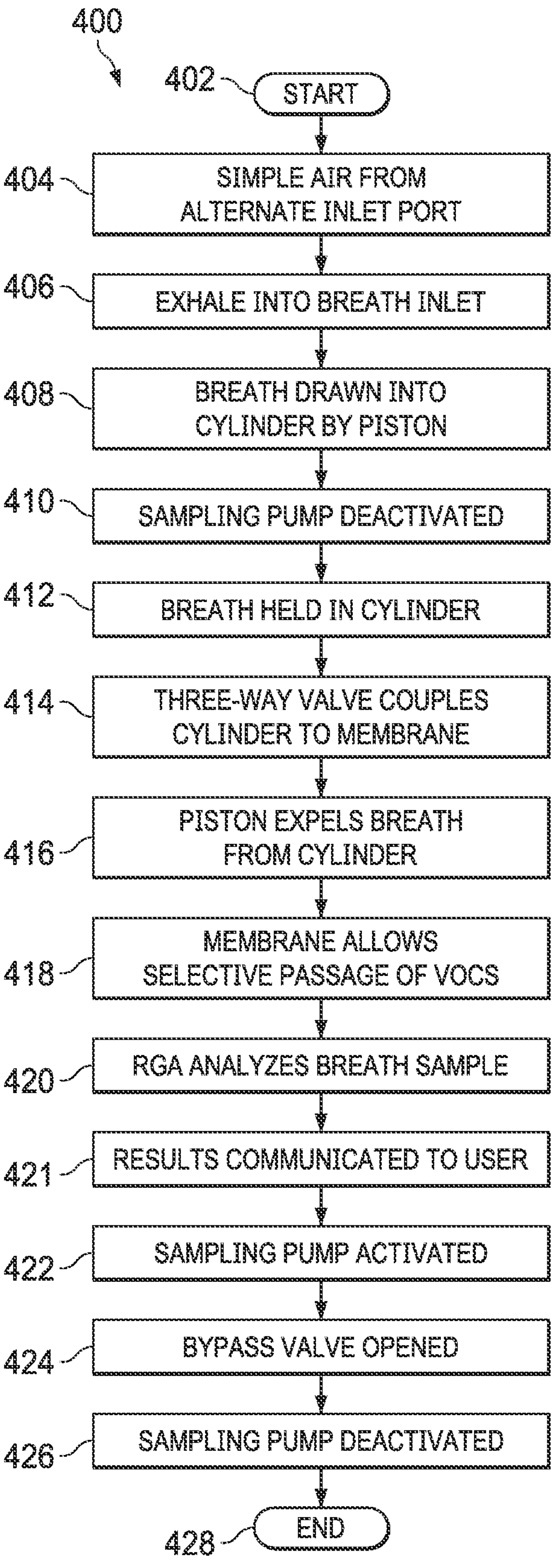
FIG. 4 is a flow diagram illustrating a process for capturing and analyzing a patient's breath according to aspects of the disclosure.

FIG. 4 is a flow diagram illustrating a process 400 for capturing and analyzing a patient's breath. The process 400 begins at step 402. At step 404, the three-way valve 216 is set to sample ambient air from the alternate inlet port 222. The bypass valve 228 is open and the sampling pump 254 is turned on. At step 406, a user checks in at the breath capture and analysis system and exhales into the breath inlet 106 through, for example, a straw. At step 408, the piston 212 is drawn down by the linear actuator 214, thereby drawing the user's exhaled breath into the cylinder 206. At step 410, the three-way valve 216 is set to sample ambient air from the alternate inlet port 222 and the sampling pump 254 is turned off. At step 412, the user's exhaled breath is held in the cylinder 206. At step 414, the three-way valve 216 is switched to allow fluid flow from the cylinder 206 to the membrane 224. At step 416, the linear actuator directs the piston 212 to push the user's breath sample out of the cylinder 206 and into the long retention time flow path 226. At step 418, the membrane 224 allows passage of VOCs through the membrane 224 and into the vacuum chamber 225. At step 420, the RGA 238 analyzes the user's breath sample. At step 421, the analysis results are delivered to the user.

The bypass valve 228, and the three-way solenoid valve 216 are connected to the alternate inlet port 222, the breath capture cylinder 206, and the membrane 224 through flow lines 218. In various embodiments, the flow lines 218 can be replaced in whole or in part with a compact block. This compact block may have ports and that connects all or some components from the bypass valve 228, and the three-way solenoid valve 216, the alternate inlet port 222, the breath capture cylinder 206, and the membrane 224. The ports in the compact block can be internally connected to facilitate the process 400 according to the flow diagram illustrated in FIG. 4.

Still referring to FIG. 4, after analysis by the RGA, a flush of the breath capture and analysis system 100 is begun. At step 422, the sampling pump 254 is turned on with the bypass valve 228 closed and the three-way valve 216 set to allow fluid flow from the cylinder 206 to the membrane 224. At step 424, the bypass valve 228 is opened and the three-way valve 216 is set to sample ambient air from the alternate inlet port 222. Step 424 returns the breath capture and analysis system 100 to the initial state. In various embodiments, if the breath capture and analysis system 100 remains idle for an extended period of time such as, for example, ten or more minutes, the process 400 proceeds to step 426 where sampling pump 254 could be turned off thereby preventing fouling of the filter 256. The process 400 ends at step 428.

Figure 5A:
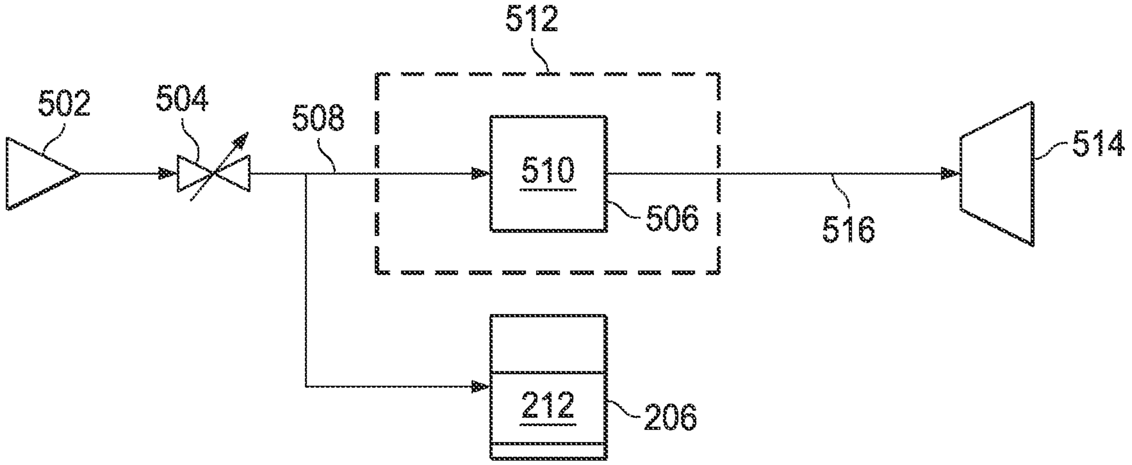
FIG. 5A is a schematic diagram illustrating a breath capture system having a concentrator according to aspects of the disclosure.
Figure 5B:
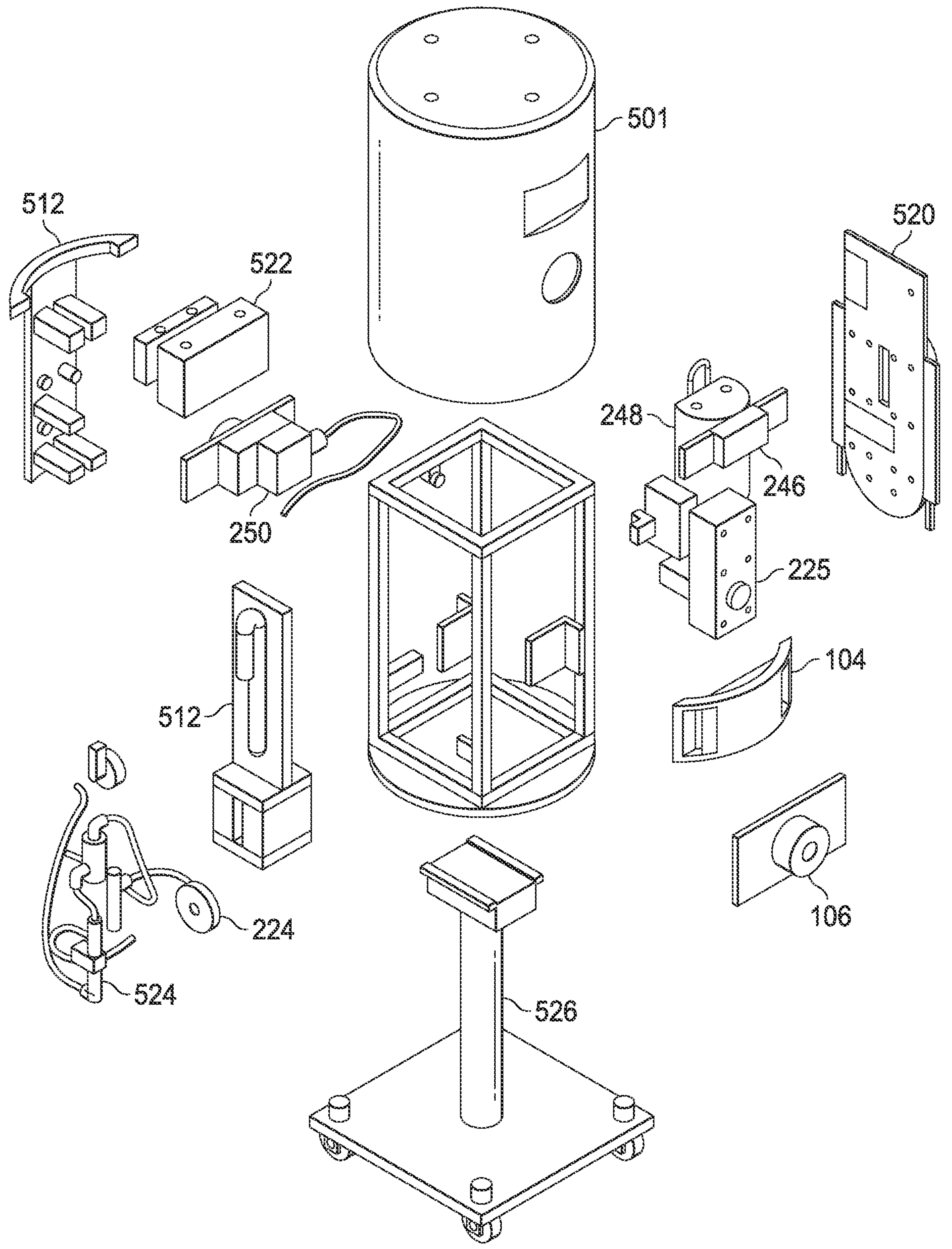
FIG. 5B is an exploded view of breath capture and analysis system having temperature control according to aspects of the disclosure.

FIG. 5A is a schematic diagram illustrating a breath capture system 500 having a concentrator 502. FIG. 5B is an exploded view of the breath capture system 500. The breath capture system 500 includes a shell 501 that conceals components of breath capture system 500. Breath capture system 500 also includes computer and electronic controls 520, power supplies 522, airflow control system 524, and an adjustable leg stand 526. The computer and electronic controls 520 provide processing power, memory, and storage for operation of breath capture system 500. A first valve 504 is fluidly coupled to an absorber 506 via a first line 508. The absorber 506 contains an absorbent 510, which has an affinity to a particular component of a gas analyte. For example, a porous polymer resin based on Poly(2,6-diphenyl-p-phenylene oxide), PPPO, (a porous polymer resin based on oxidative polymerisation of 2,6-diphenylphenol, known by its trademark Tenax TA) could be used as an absorbent. This sorbent is selective based on breakthrough volume data to Aldehyde Octanal 1400:0.035 relative to water at 40 C. At 140 C the breakthrough volume is only 0.5 L/g indicating desorption. In various embodiments, Tenax TA has selective affinities for Alcohols, Alkenes, Acetates, Aldehydes, Ketones, Aromatics, and Amines. These sorbents can be placed within a temperature-controlled analyte volume. Breath passed over the sorbent directly or after transmission through a membrane can trap when cold, and release when heated. With valve switching to remove other gases, and direct flow of desorbed VOC this may be programmatically released at a specific time and at intense ~100 fold increased concentration to the detector. In other embodiments, another appropriate sorbent to be used in conjunction is, for example, a carbon molecular sieve such as, for example, those known by the trade names Carboxen 569 and Carbotrap C. These sorbents have higher cycling temperatures and are only absorbent to a subset of those compounds which Tenax TA absorbs. Placed in a separate analyte volume and programmatically heated and cooled this can add another dimension of data to the analysis platform. In various embodiments, the absorber 506 is thermally exposed to a thermal-management system 512. The thermal-management system 512 is capable of varying the temperature of the absorbent 510 that is contained in the absorber 506. In various embodiments, the thermal-management system 512 may raise or lower the temperature of the absorbent 510. In various embodiments, the thermal management system 512 may raise or lower the temperature of the membrane 224 and the vacuum chamber 225. In such embodiments, the absorber 506 may be omitted or embedded into the structure of the membrane material. For example, in various embodiments, a polydimethylsiloxane (PDMS) membrane could be utilized. In various embodiments, increasing or decreasing at least one of a temperature or a pressure of the absorbent 510 may alter the affinity of the absorbent 510. Examples of affinity variance with temperature for various compounds are illustrated in Table 1. That is, the component of the gas analyte to which the absorbent 510 exhibits affinity may be adjusted by changing at least one of the temperature or the pressure of the absorbent 510 via the thermal-management system 512.

TABLE 1

| | | Breakthrough Volume Data Liter per gram | | | | | | | | |
|---|---|---|---|---|---|---|---|---|---|---|
| Temperature | Sorbent | 0 | 20 | 40 | 60 | 80 | 100 | 120 | 140 | 160 |
| 1-Propanol | Tenax TA | 63 | 11 | 2.68 | 0.695 | 0.203 | 0.063 | 0.026 | 0.012 | 0.006 |
| 1-Propanol | Carboxen 569 | 20 | 12 | 8 | 5 | 2.6 | 1.5 | 0.8 | 0.46 | 0.26 |
| Water | Tenax TA | 0.13 | 0.065 | 0.035 | 0.018 | 0.01 | 0.006 | 0.004 | 0.002 | 0.001 |
| Benzene | Tenax TA | 410 | 70 | 18 | 8.1 | 0.86 | 0.268 | 0.099 | 0.04 | 0.018 |
| Benzene | Carboxen 569 | 130 | 85 | 53 | 33 | 21 | 14 | 9 | 5.4 | 3.3 |
| n-Heptylamine | Tenax TA | 56000 | 5000 | 560 | 78 | 17 | 4 | 1 | 0.32 | 0.101 |
| Acetone | Tenax TA | 28 | 6 | 1.4 | 0.4 | 0.127 | 0.047 | 0.019 | 0.009 | 0.004 |
| 2-Butanone | Tenax TA | 251 | 40 | 7.1 | 1.9 | 0.483 | 0.151 | 0.058 | 0.023 | 0.009 |
| Acetic Acid | Tenax TA | 28 | 5.6 | 1.4 | 0.427 | 0.137 | 0.045 | 0.017 | 0.008 | 0.004 |
| 1-Pentene | Tenax TA | 25 | 4.5 | 1 | 0.263 | 0.085 | 0.031 | 0.012 | 0.005 | 0.002 |

Still referring to FIGS. 5A-5B, a pump 514 is fluidly coupled to the absorber via a second line 516. The piston 212 is fluidly coupled to the first line 508. The analytical system 204 is fluidly coupled to the breath capture system 202 downstream of the pump 514.

Figure 6A:
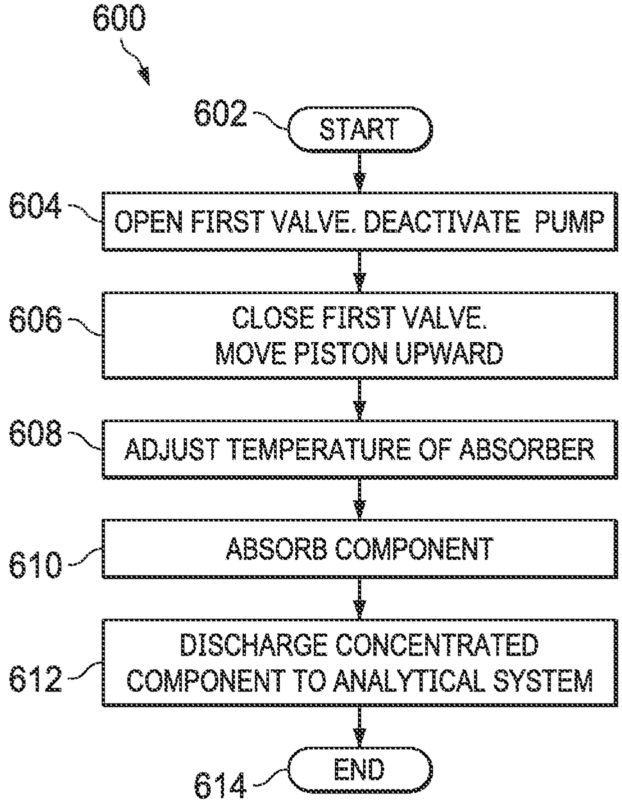
FIG. 6A is a flow diagram illustrating a process for capturing and concentrating a breath sample according to aspects of the disclosure.

FIG. 6A is a flow diagram illustrating a process 600 for capturing and concentrating a breath sample. The process begins at step 602. At step 604, the first valve 504 is open and the pump 514 is deactivated. The piston 212 is moved downwardly to facilitate a breath of the user being drawn into the cylinder 206. At step 606, the first valve 504 is closed and the piston 212 is moved upwardly in the cylinder 206 thereby expelling the captured breath into the absorber 506. At step 608, the temperature of the absorber 506 is adjusted using the thermal-management system 512. Adjustment of the temperature of the absorbent 506 changes the affinity of the absorbent and may change the specific component of the gas analyte that is detected. At step 610, a specific component of the breath is absorbed by the absorbent 510. In various embodiments, steps 604-610 may be repeated. In various embodiments, capturing the specific component with the absorbent 510 increases the concentration of the component to levels that are detectable by the analytical system 204. At step 612, the pump 514 is activated and the concentrated sample is drawn out of the absorber and into the analytical system 204. In various embodiments, during step 612 the temperature of the absorbent 510 is decreased to a temperature below a threshold where the breakthrough volume is high. In this case the breakthrough volume is the volume of carrier gas (in liters) that will remove an analyte from one gram of sorbent. Other things being equal, breakthrough volume greater than one indicates more absorption and less than one more desorption. Then the breath or preconcentrated breath is passed through the absorbent 510. The system is sealed. The temperature of the absorbent 510 is increase to a threshold where the breakthrough volume for a specific compound is low then the analyte volume is opened to either an additional serial concentrating step or to the analytical system 204. The temperature may be reduced to as low as 1° C. The temperature may be increase to as high as 150° C. or 250° C. depending on the degradation temperature of the absorbent 510 and or membrane. The process 600 ends at step 614.

Figure 6B:
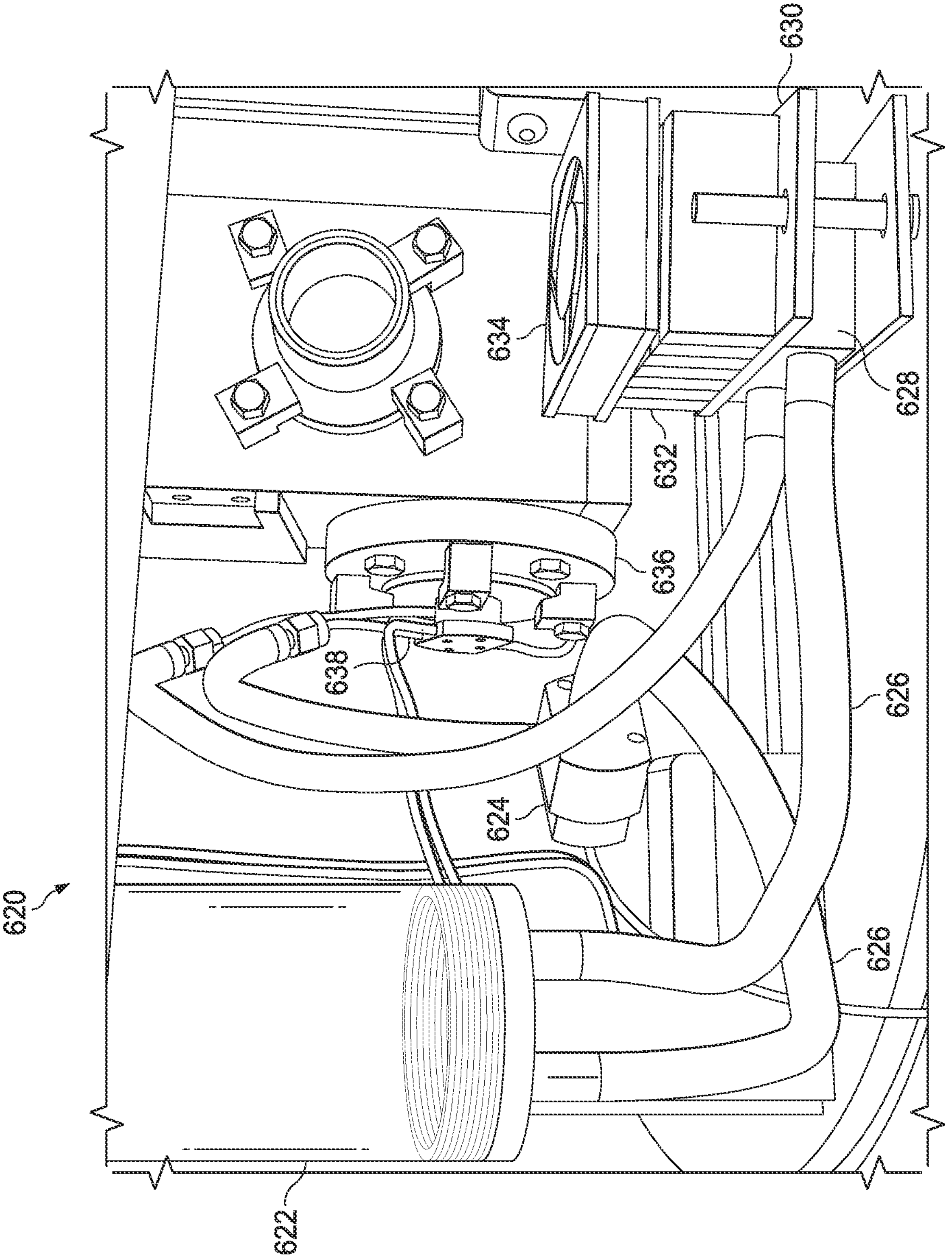
FIG. 6B is a liquid cooling and heating system that enables rapid temperature changes of the membrane according to aspects of the disclosure.

FIG. 6B is a membrane assembly 620 that provides rapid cooling and heating. The membrane assembly 620 includes a liquid coolant reservoir 622, a pump 624, tubes 626 for circulating fluid, a water block 628, a Peltier module 630 (thermoelectric cooler), a finned heat sink 632, a cooling fan 634, a membrane subassembly 636, and a heater 638. The Peltier module 630, when active, provides cooling to the fluid and heater 638, when active, provides heating to the fluid. In various embodiments, the membranes assembly is a chilled-water cooled and resistively heated selective membrane assembly. In various embodiments, the membrane assembly is capable of +150° C./min and −150° C./min temperature swings in the range of −10° C. to 200° C. Fast temperature ramping is necessary for rapid breath analysis and diagnosis.

Referring again to FIG. 6A, use of the absorbent 510 enables concentration of components that are present in amounts that are too small to be detected by the analytical system 204. Thus, use of the absorbent 510 increases the sensitivity of the analytical system 204 and allows detection of low concentrations of components. In various embodiments, the components could be, for example, airborne chemical species, metabolites, or pathogens present in an airstream. Such capability allows detection of components at concentrations below the detection limit of many detectors.

Figure 7:
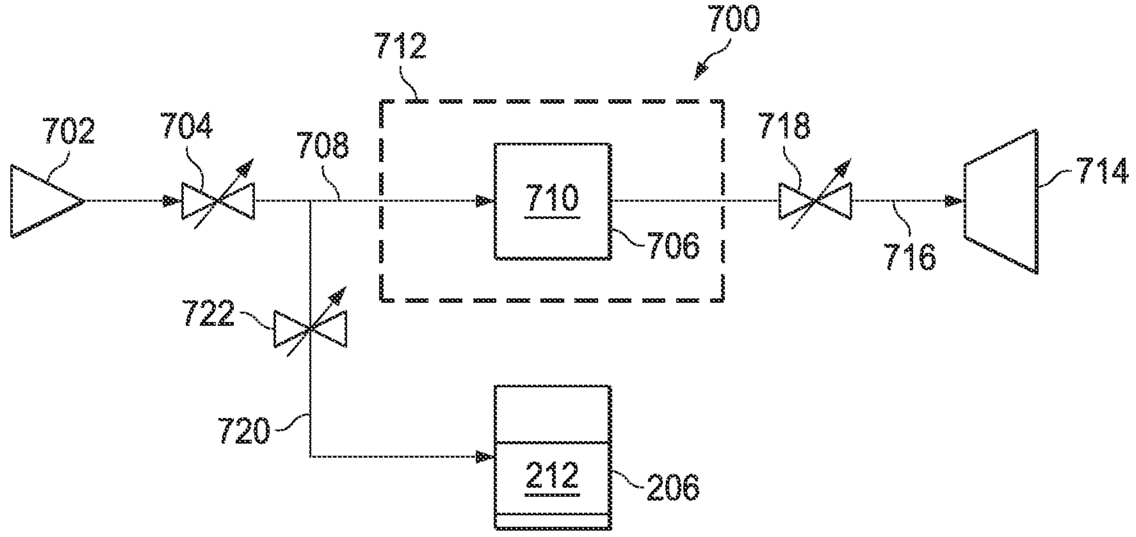
FIG. 7 is a schematic diagram illustrating a breath capture system having a concentrator according to aspects of the disclosure.

FIG. 7 is a schematic diagram illustrating a breath capture system 700 having a concentrator 702. The breath capture system 700 includes a first valve 704. The first valve 704 is fluidly coupled to an absorber 706 via a first line 708. The absorber 706 contains an absorbent 710, which has an affinity to a particular component of a gas analyte. In various embodiments, the absorber 706 is thermally exposed to a thermal-management system 712. The thermal-management system 712 is capable of varying the temperature of the absorbent 710 that is contained in the absorber 706. In various embodiments, increasing or decreasing at least one of a temperature or a pressure of the absorbent 510 may alter the affinity of the absorbent 710. That is, the component of the gas analyte to which the absorbent 710 exhibits affinity may be adjusted by changing at least one of the temperature or the pressure of the absorbent 710 via the thermal-management system 712.

Still referring to FIG. 7, a pump 714 is fluidly coupled to the absorber 706 via a second line 716. A second valve 718 is disposed in the second line 716 between the absorber 706 and the pump 714. The piston 212 is fluidly coupled to the first line 708 via a third line 720. A third valve 722 is disposed in the third line 720. The analytical system 204 is fluidly coupled to the breath capture system 700 via the cylinder 206.

Figure 8:
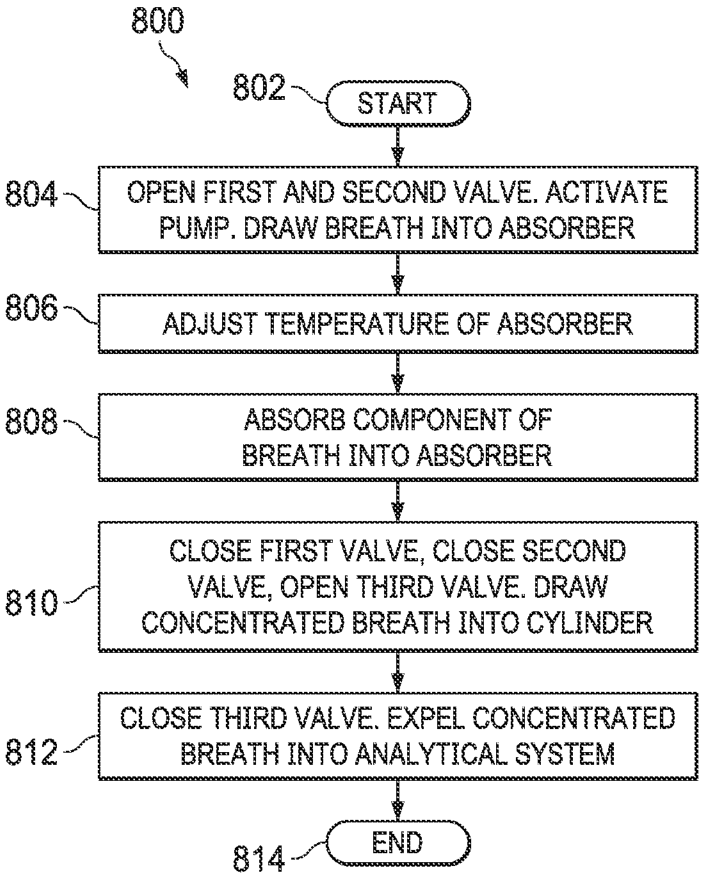
FIG. 8 is a flow diagram illustrating a process for capturing and concentrating a breath sample according to aspects of the disclosure.

FIG. 8 is a flow diagram illustrating a process 800 for capturing and concentrating a breath sample. The process 800 begins at step 802. At step 804, the first valve 704 is open, the second valve 718 is open, the third valve 722 is closed, and the pump 714 is activated. The pump 714, draws a user's breath into the absorber 706. At step 806, the temperature of the absorber 706 is adjusted using the thermal-management system 712. Adjustment of the temperature of the absorbent 710 changes the affinity of the absorbent 710 and may change the specific component of the gas analyte that is detected. At step 808, a specific component of the breath is absorbed by the absorbent 710. In various embodiments, capturing the specific component with the absorbent 710 increases the concentration of the component to levels that are detectable by the analytical system 204.

Still referring to FIG. 8, at step 810, the first valve 704 is closed, the second valve 718 is closed, and the third valve 722 is opened. The piston 212 is moved downwardly to facilitate drawing the concentrated sample into the cylinder 206. At step 812, the third valve 722 is closed and the piston 212 is moved upwardly to expel the concentrated sample to the analytical system 204. The process 800 ends at step 814.

Still referring to FIG. 8, use of the absorbent 710 enables concentration of components that are present in amounts that are too small to be detected by the analytical system 204. Thus, use of the absorbent 710 increases the sensitivity of the analytical system 204 and allows detection of low concentrations of components. In various embodiments, the components could be, for example, airborne chemical species, metabolites, or pathogens present in an airstream. Such capability allows detection of components at concentrations below the detection limit of many detectors.

Figure 12:
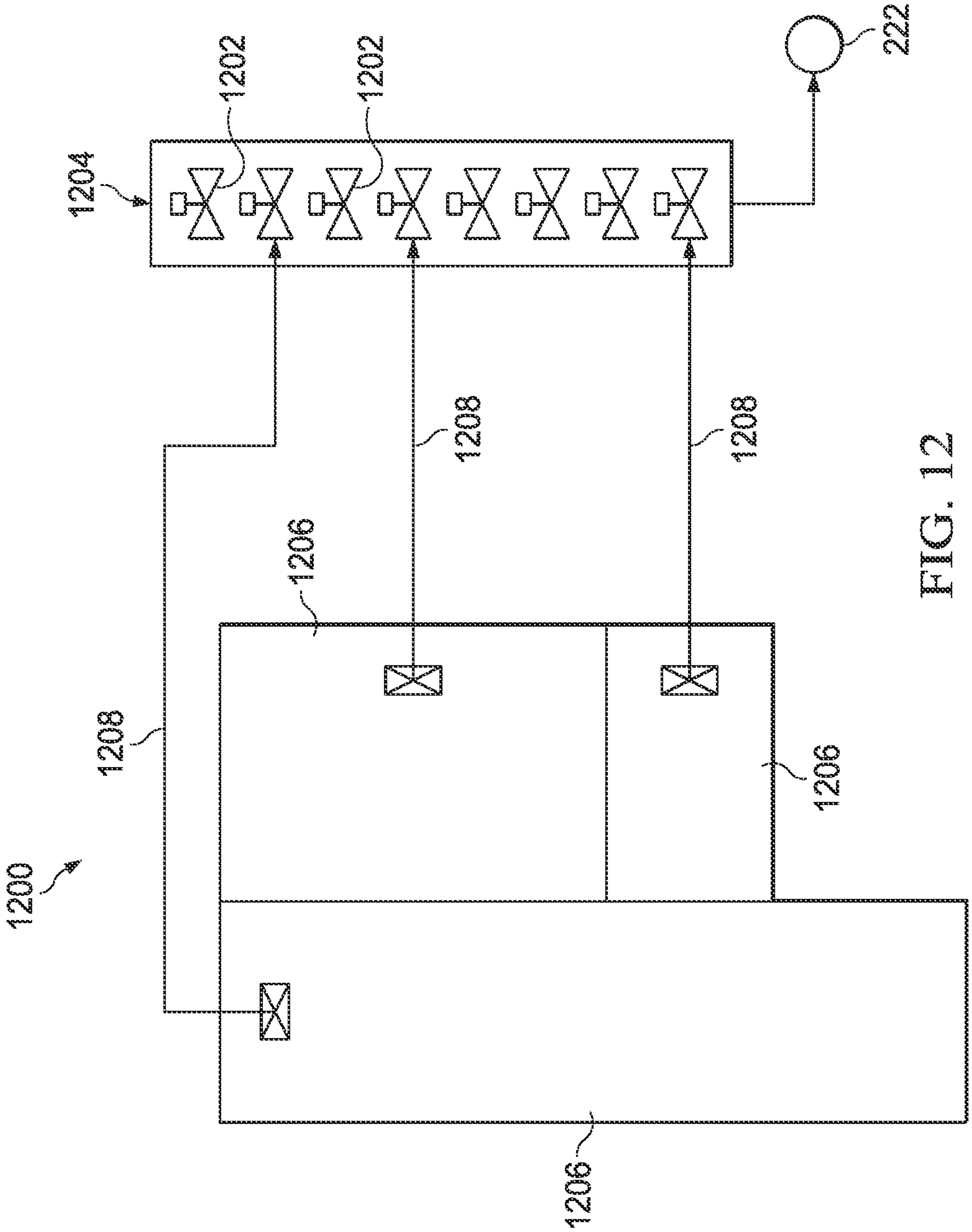
FIG. 12 is a pool sampling mechanism that can be attached to an inlet port according to aspects of the disclosure.

The retention time in the flow path 226 adjacent to the membrane is such that the concentration of the VOC entrained in the gas flow is maintained at a high level over the absorbent 510, 710 or membrane 224 for a duration in excess of the characteristic time of elution of the VOC into the membrane 224. That characteristic time is temperature, species, and membrane material dependent. For example, for a 0.08 mm thick platinum cured PDMS (Poly-dimethylsiloxane) membrane at 100° C. the characteristic time to reach 90% of maximum concentration for acetone through the membrane is 65 seconds. In another example, for a 0.1 mm thick PDMS membrane at 30° C. the time to reach 90% of maximum concentration for isoprene is only 15 seconds. In a third example a membrane can be initially maintained at 30° C. for a duration of 20 seconds, spiked by heating to a temperature of 120° C. over a duration of 30 seconds, held at 120° C. for 20 seconds then rapidly cooled to 30° C. over a duration of 30 seconds. VOC laden flow should be retained for the initial 70 seconds, then rapidly replaced with clean air for the remainder. Such programmatic flow retention and temperature control can result in an isoprene peak followed 10 s of seconds later by a spike of acetone signal (larger than that achievable with a constant temperature membrane). The flow path should also be such that the membrane interface is well mixed such that local concentrations of VOC are not depleted and favorable concentration gradients are maintained at interfaces for the desired duration. The amount of VOC which is preferentially adsorbed onto and absorbed into the material is also proportional to the contact area between the VOC containing flow and membrane or sorbent materials. A larger surface area thus increases the amount of VOC transmitted to the detector. The detector and/or vacuum system may have an upper limit on the amount of transmitted VOC and air components, and too large an area may cause undesirable operation. For example, a 3 $cm^2$ membrane can transmit VOC and maintain an RGA detector pressure of 2E-5 torr, whereas a 100 $cm^2$ membrane transmits more VOC but the same vacuum system can only maintain a pressure of 6E-4 Torr. Detector sensitivity is pressure and concentration dependent and an optimal may be an intermediate surface area. As an alternative optimization configuration, a 100 $cm^2$ membrane may be place in series with a 3 $cm^2$ membrane in serial flow path configurations to transmit more VOCs to the detector while still maintaining a lower pressure. The flow path 226 in the intermediate stage between the membranes, similar to the case for a single membrane can have an optimized temperature and retention time profile. The timing and area have multiple constraints related to the system operation. In patient screening for disease such as COVID-19 high throughput, highly targeted testing on the order of 2 minutes per patient can be desirable and achieved at the by sacrificing high sensitivity to a broader range of VOC compounds. In non-emergency screening of patients for broader health concerns or environmental exposure testing cycles on the order of 6 minutes per patient might be appropriate and necessary to detect at higher fidelity a broader range of exposure and disease. Similarly pool or aggregate sampling of multiple subjects in a shared space by indirect sampling of the room or ventilation system exhaust may benefit from highly targeted but longer (~10 min) sample retention times. FIG. 12 shows a pool sampling mechanism 1200 that can be attached to the alternate inlet port 222 as an external attachment. The pool sampling mechanism 1200 includes a plurality of solenoid valves 1202 disposed within a multi-space manifold 1204. The multi-space manifold 1204 receives air samples from a plurality of spaces 1206 via exhaust ducts 1208. The solenoid valves 1202 may be configured as either open or closed as desired to direct the air samples from the plurality of spaces 1206 as desired to an inlet (e.g., inlet ports 106 or 222) for analysis.

Figure 11:
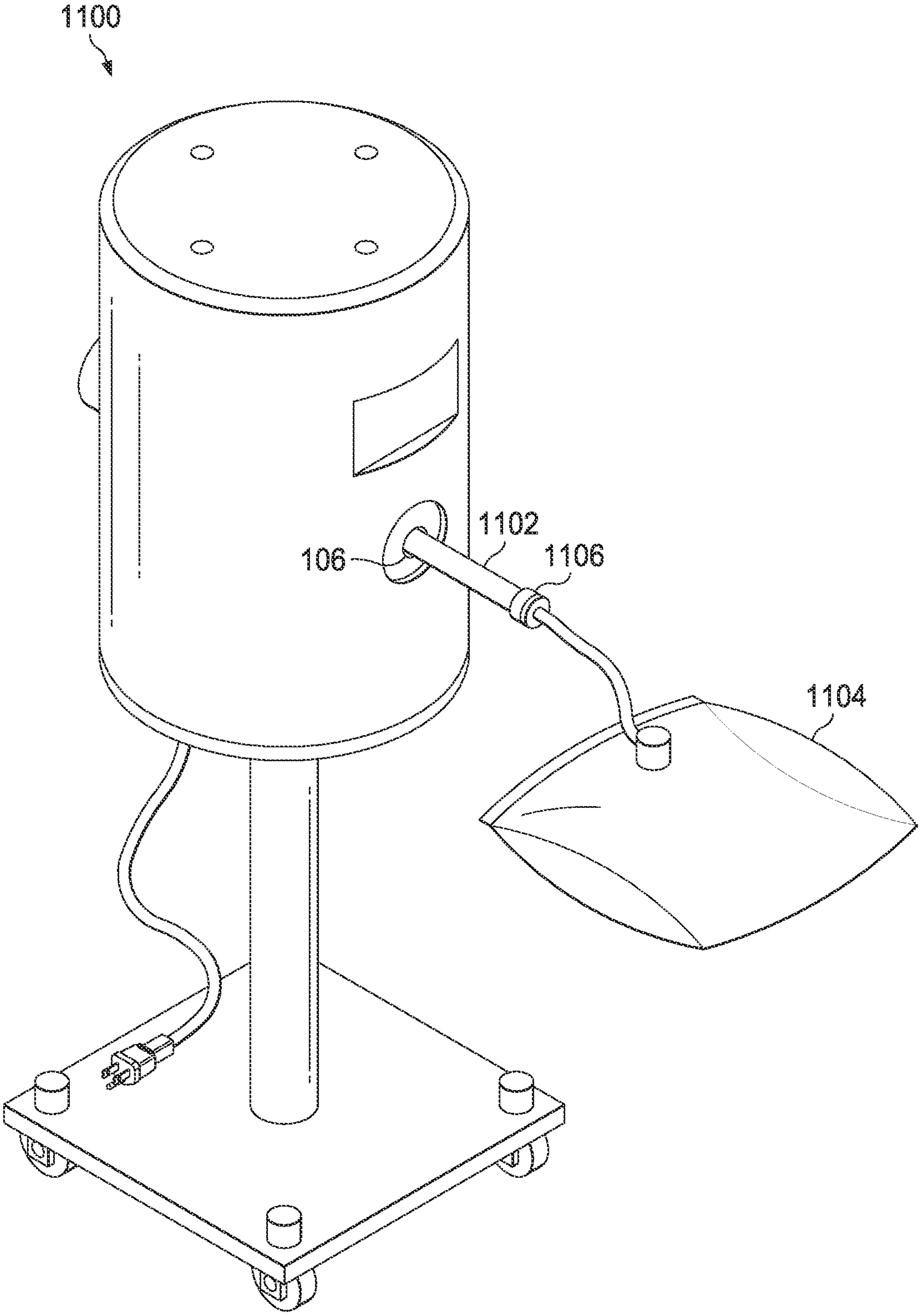
FIG. 11 is a push fit pipe attachment for analyte sample injection using gas sampling bags for calibration purpose according to the aspects of the disclosure.

FIG. 11 is a demonstration of a pipe push fit system 1100 to facilitate leakage free calibration of the machine. The pipe push fit system includes an external pipe connection 1102 attached to the inlet port 106, where a gas sampling bag 1104 can be connected via push fitting mechanism 1106. Various analytes including but not limited to Acetone, Benzene, Xylene, Methyl Salicylate (MeS), Decenal, Isoamyl Acetate (IaA) can be filled in the gas sampling bag 1104 and injected through the push fit system 1100.

Figure 9:
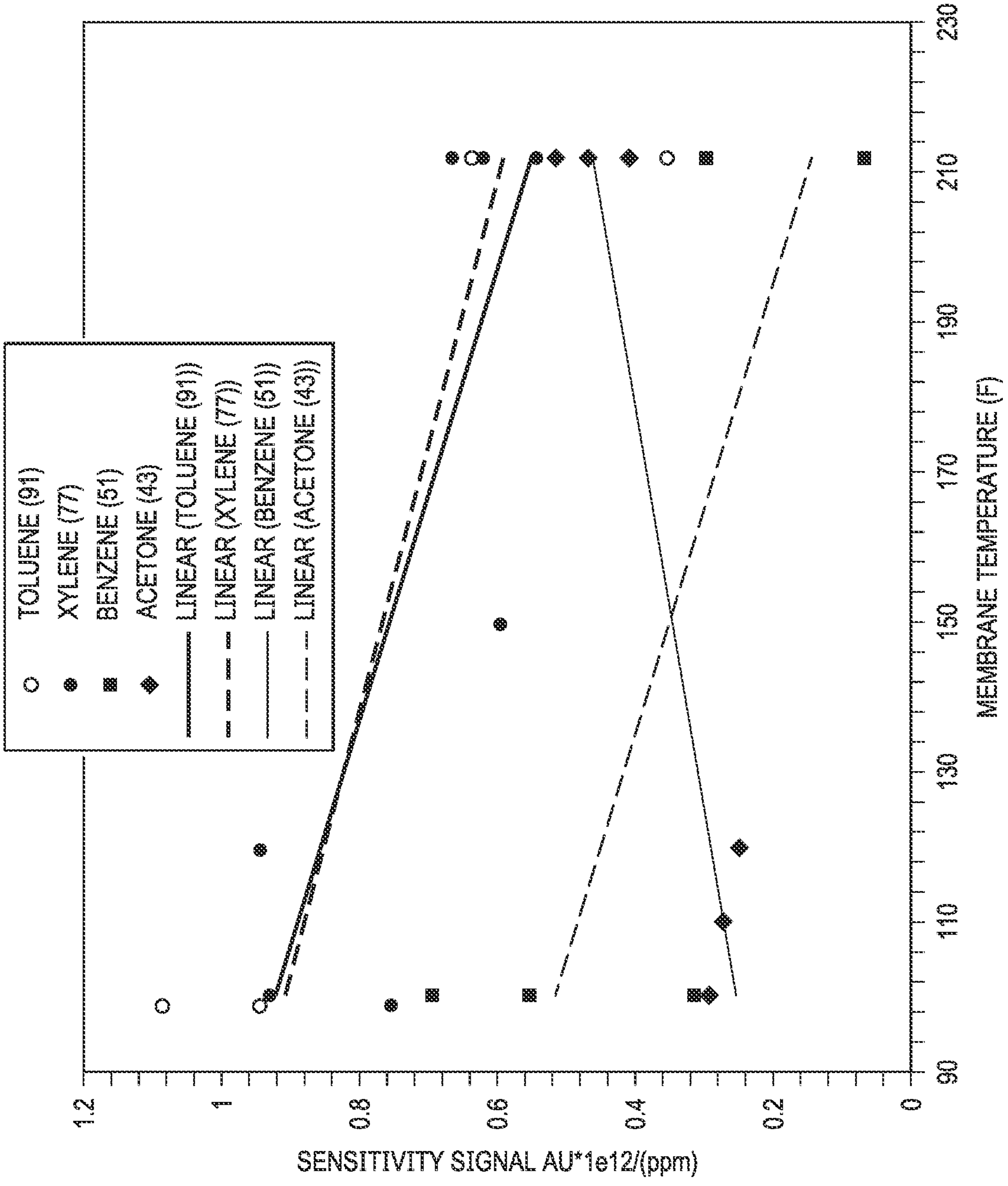
FIG. 9 is a graph illustrating membrane sensitivity according to aspects of the disclosure.
Figure 10:
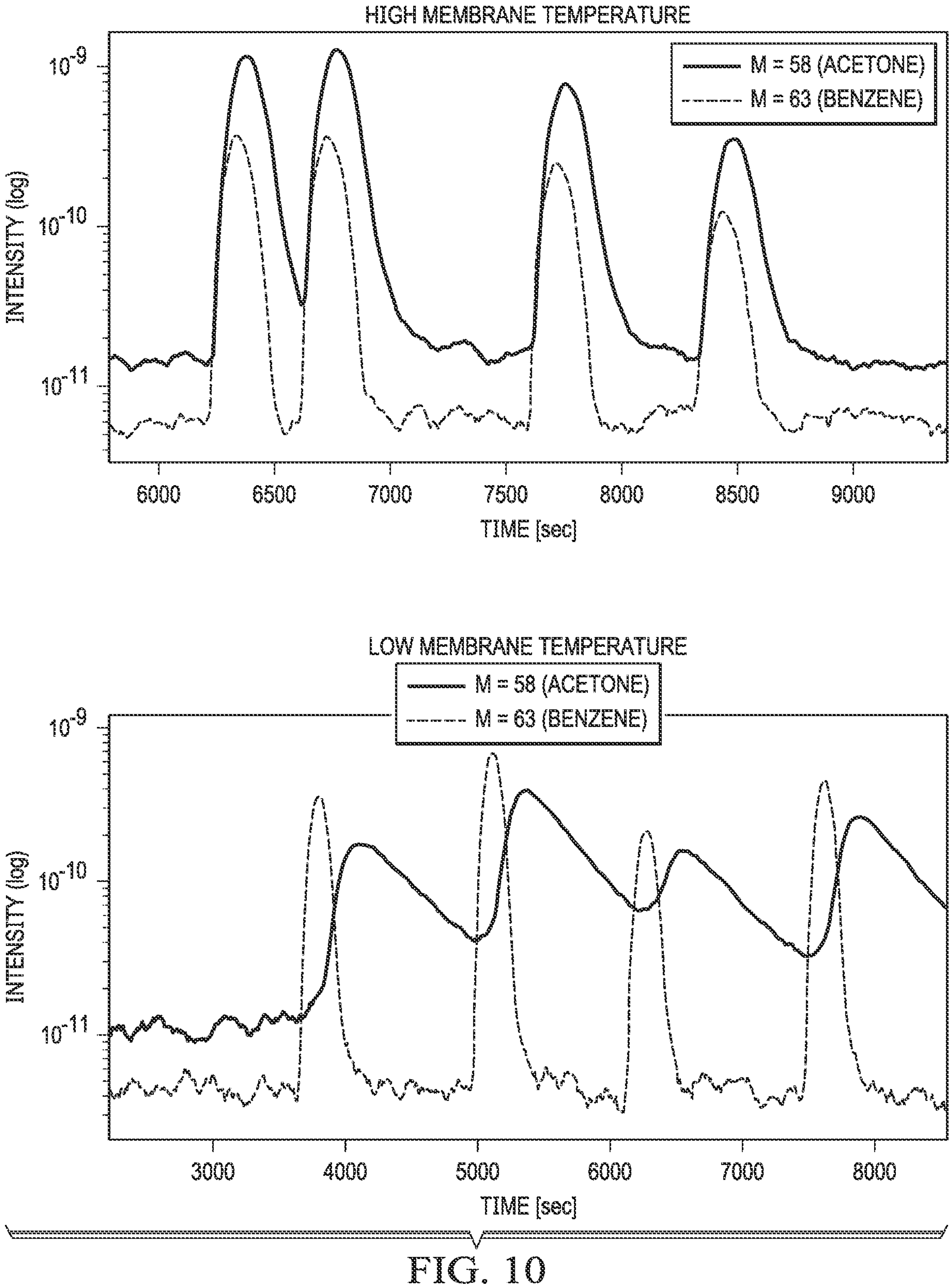
FIG. 10 is an experimentally obtained graph showing membrane sensitivity with varying temperatures according to the aspects of the disclosure.

FIG. 9 is a graph illustrating membrane sensitivity as a function of temperature. As illustrated, compounds such as, for example, Toluene, Xylene, and Acetone exhibit decreased membrane sensitivity at higher temperatures while compounds such as, for example, Benzene, exhibit increased membrane sensitivity at higher temperatures. FIG. 10 is an experimentally obtained graph demonstrating membrane sensitivity with varying temperatures. Known quantities of the compounds Acetone and Benzene were injected into the gas sampling bags filled with air.

Figure 13:
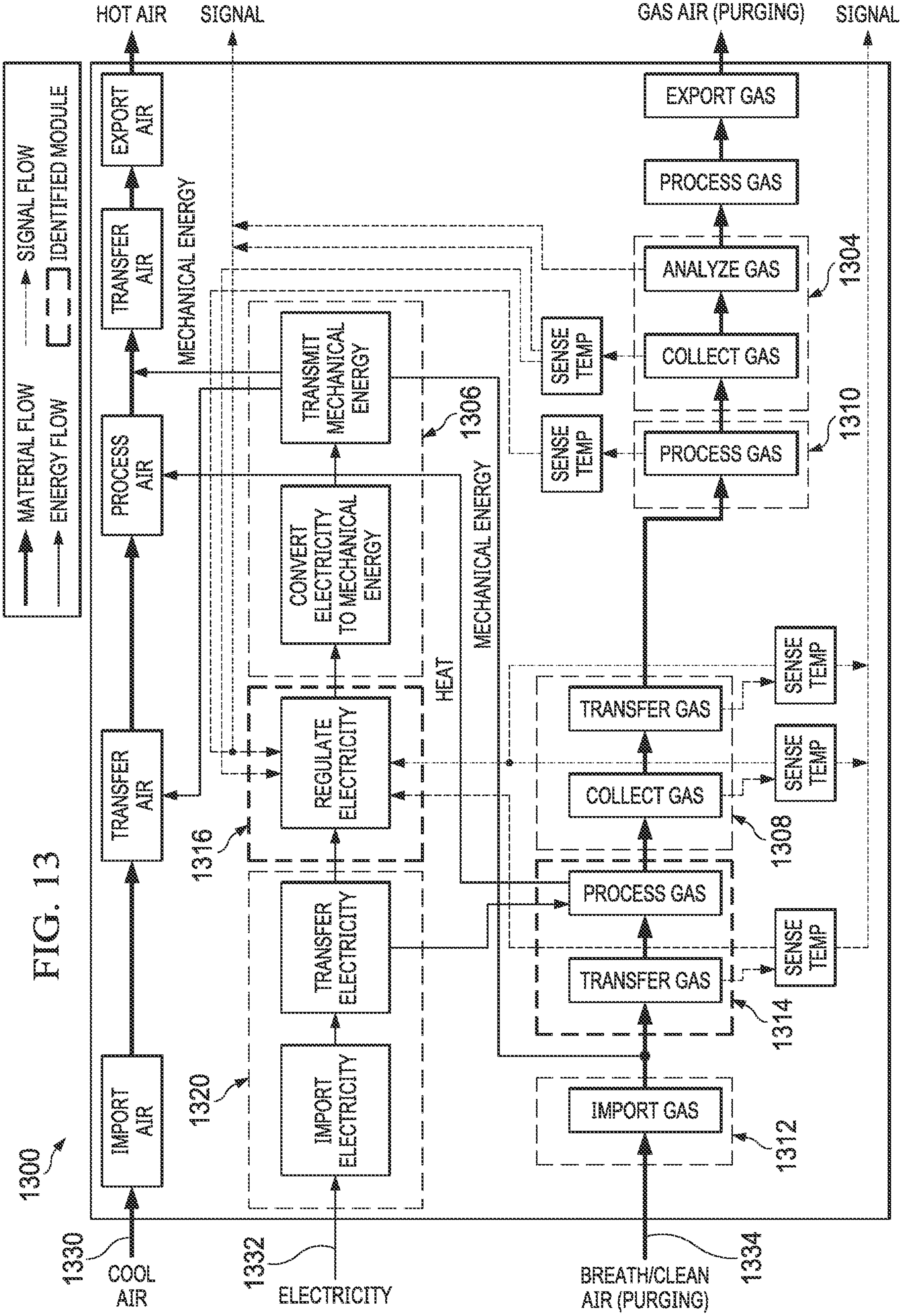
FIG. 13 is a functional model of a breathanalyzer system according aspects of the disclosure.

FIG. 13 is a functional model of a breathanalyzer system 1300 according aspects of the disclosure. Breathanalyzer system 1300 is an exemplary implementation of system 100 according to aspects of the disclosure. Breathanalyzer system 1300 includes a frame subassembly (an example of the frame subassembly is best seen in FIG. 5B), a mass spectrometer and vacuum chamber subassembly 1304, a roughing pump subassembly 1306, a breath capture system subassembly 1308, a membrane subassembly 1310, an inlet subassembly 1312, an air-flow subassembly 1314, an electronics control monitoring panel subassembly 1316, a power supply subassembly 1320, a display subassembly (an example of the frame subassembly is best seen in FIG. 5B as interface 104), a shell subassembly (an example of the shell subassembly is best seen in FIG. 5B as shell 510, and a leg subassembly (an example of the leg subassembly is best seen in FIG. 5B). Each subassembly could be assembled in parallel and sequentially put together to build the whole assembly of system 1300. Some simpler subassemblies in system 1300 are frame subassembly and subassemblies 1324 and 1326, which provides structural support, a protective cover, and an up-down movement to system 1300, respectively. A user's breath is collected via subassembly 1312. Subassembly 1312 is made from copper, which helps sanitize the exposed surfaces of the inlet. The breath (or clean air during the purging cycle) then travels through an air-flow system to reach subassembly 1308. Subassembly 1308 includes a piston-cylinder mechanism actuated by a linear actuator and helps capture a large volume of breath air from the patient and provides a pressurized injection of the breath into subassembly 1304. The breath gets filtered through subassembly 1310 before entering subassembly 1304. Subassembly 1316 includes electrical connections to actuators, temperature controllers, heaters, pumps, mass spectrometer, and other accessories of system 1300, and also accommodates an on-board computing unit, cooling fans, general-purpose input/output (GPIO) boards, and relays. Table 2 includes further description of each of the subassemblies of system 1300.

TABLE 2

List of subassemblies in breathanalyzer system 1300 and a description of their functions.

| Module Number | Subassembly | Description |
|---|---|---|
| 1302 | Frame subassembly | Provides structural support to other subassemblies |
| 1304 | Mass spectrometer and vacuum chamber sub-assembly | Includes a vacuum chamber, a turbo pump, a mass spectrometer (RGA), and a Pirani gauge. The detection of chemicals in the breath is carried out in the vacuum chamber using the mass spectrometer. |
| 1306 | Roughing Pump Assembly | The roughing pump is a diaphragm pump that helps generate an initial vacuum (up to 1 torr) inside the vacuum chamber. |
| 1308 | Breath Capture System (BCS) | BCS is a piston-cylinder arrangement operated by a linear actuator. The purpose of BCS is to pressurize the breath air before filtering through the membrane. |
| 1310 | Membrane sub-assembly | The membrane assembly mainly supports a polydimethylsiloxane (PDMS) membrane that filters out unnecessary compounds from the breath sample before sending it to the vacuum chamber. |
| 1312 | Inlet subassembly | It includes a copper receptor that collects breath air sample and transfers to the air flow system. |
| 1314 | Air-flow sub-assembly | The air-flow assembly includes a bypass valve, a three-way solenoid valve, two check valves, a sampling pump, and copper piping. The function of this subassembly is to facilitate and direct the flow of the breath sample and clean air during sampling and purging cycles. |
| 1316 | Electronics control and monitoring panel subassembly | The electronics control subassembly accommodates relay switches, controllers, GPIO board, cooling fans, an on-board computer, and other electronic components. The monitoring panel subassembly includes temperature controllers that control temperatures of 5 components (BCS, Inlet, Membrane, Vacuum Chamber, Air-flow system). |
| 1320 | Power supply sub-assembly | The power supply subassembly converts 110 V AC into 24 V and 12 V DC power. |
| 1322 | Display subassembly | The display subassembly includes an LCD screen that facilitates human-machine interactions. |
| 1324 | Shell subassembly | The shell subassembly provides a protective and aesthetic cover to the kiosk. |
| 1326 | Leg subassembly | The leg subassembly helps adjust the height of the kiosk while sampling. |

Functional modeling of the system 1300 is shown in FIG. 13. There are three primary function chains 1330, 1332, and 1334. Function chain 1330 is associated with breath capturing and analysis. Function chain 1330 starts with receiving the breath of the patient, which is indicated by the function import gas performed by subassembly 1312. Then the breath is transferred and heated along the way in subassembly 1314. The functions of the air-flow system are described by transfer gas and process gas. Next, the breath proceeds to subassembly 1308, where the breath is collected (collect gas) and transferred further (transfer gas). The breath is then filtered through a heated silicone membrane of subassembly 1310 and is collected in the vacuum chamber of subassembly 1304 to be analyzed by an RGA. The functions process gas, collect gas, and analyze gas represent the operations of the membrane, vacuum chamber, and RGA.

After analyzing the breath, it is filtered by an N95 respirator filter (process gas) and then exhausted in the environment (export gas). During the purging cycle, the same function chain represents the purging operation with the only difference being clean air is imported in place of human breath. Function chain 1332 performs broad functions of cooling the equipment within the breathalyzer kiosk. The cooling fans import air (cool air), transfer air, process air (heat transfer) and then export air (hot air) to the atmosphere. Function chain 1334 imports, and controls electricity. The vacuum chamber, inlet module, membrane, BCS, and air-flow system have temperature sensors, which provide feedback signal to control their temperatures.

Figure 14B:
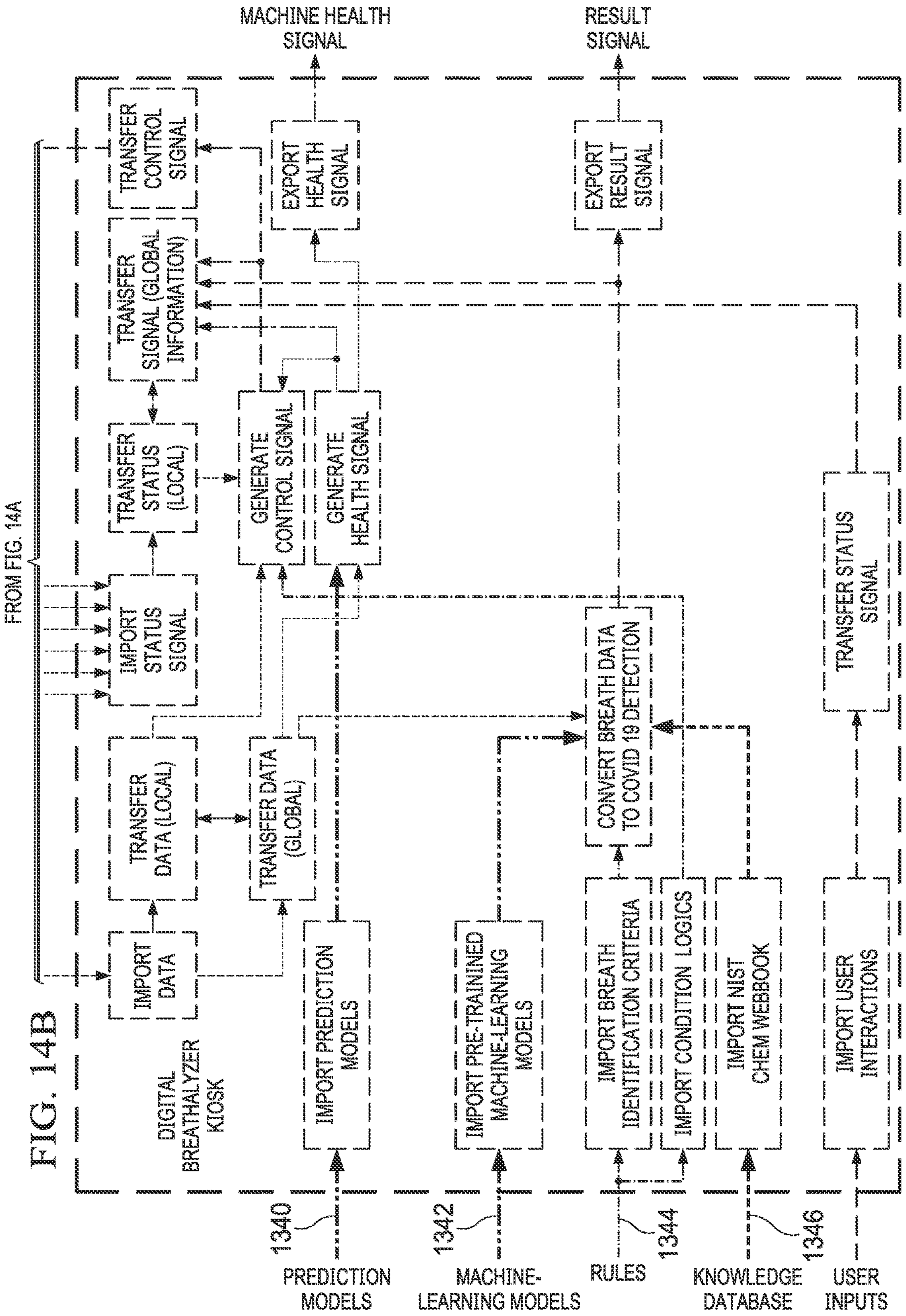
FIG. 14 illustrates the operation of the breathanalyzer system of FIG. 13 according to aspects of the disclosure.

FIG. 14 illustrates the operation of system 1300 according to aspects of the disclosure. For example, FIG. 14 illustrates operation of system 1300 as carried out by a central processing unit. In addition to the functions described for 1300, models 1340, models 1342, rules 1344, and knowledge databases 1346 are imported. Specifically, rule-based models for controlling devices such as RGA, pumps, temperature controllers, heaters, and relays, identification criteria for detecting breath signals; NIST Chem webbook for the chemical information, COVID-19 biomarker information; machine learning models that compare the breath signals with the biomarkers, and predictive models for machine health monitoring are imported.

The status of the devices and equipment (e.g., heaters, RGA, Turbopump, etc.) is stored locally. In our case, the local storage and computing is performed on an on-board computing unit (e.g., an on-board computing unit that includes a central processing unit, memory, and storage). This can be replaced with a local edge device. The RGA continuously records the mass spectroscopy data, which is first stored locally and then transferred to the cloud storage. The equipment status data is transferred to a cloud (global) storage frequently. The user can interact with the global data via a remotely accessible interface. The user can observe the real-time health and equipment status information and feed decisions via the interface. When the user accesses the system remotely, the user inputs are first stored globally and transferred to the local device at regular time intervals. The device control logics, the current health of the equipment, user-inputs, and sensor data are transferred to the local computing unit that generates control signals and relays to the respective equipment or devices.

With continuously recorded breath data, breath identification rules, NIST Chem webbook, knowledge related to COVID-19 biomarkers, and pre-trained ML models, the digital twin (DT) predicts the COVID-19 positive or negative results for subjects. The user can obtain the results on the globally accessible user interface.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially," "approximately," "generally," and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an," and other singular terms are intended to include the plural forms thereof unless specifically excluded.

What is claimed is:

1. A breath capture and analysis system comprising:
- a breath inlet coupled to a cylinder;
- a piston disposed in the cylinder, the piston being actuated by an actuator;
- a flow path coupled to the cylinder;
- a selective media exposed to the flow path, the selective media comprising a membrane configured to selectively permeate volatile organic compounds therethrough from the flow path at a first pressure to the vacuum chamber at a second pressure lower than the first pressure;
- a vacuum chamber coupled to the selective media;
- a detection mechanism disposed in the vacuum chamber, wherein the detection mechanism is a residual gas analyzer comprising: an ionizer; a quadrapole; a signal multiplier;
- and a signal detector, the residual gas analyzer being configured to operate at the second pressure; and
- a pump coupled to the vacuum chamber.

2. The breath capture and analysis system of claim 1, comprising:
- a sampling pump fluidly coupled to the flow path and to the cylinder; and
- a bypass exhaust coupled to the sampling pump.

3. The breath capture and analysis system of claim 1, comprising:
- a long retention time flow path coupled to the vacuum chamber; and
- a three-way valve selectively coupling the long retention time flow path to the cylinder and to an alternative inlet port.

4. The breath capture and analysis system of claim 3, comprising:
- a bypass flow line bypassing the long retention time flow path; and
- a bypass valve disposed in the bypass flow line.

5. The breath capture and analysis system of claim 1, wherein the breath inlet is constructed of copper.

6. The breath capture and analysis system of claim 1, wherein the breath inlet and the cylinder are heated.

* * * * *